United States Patent [19]

Takamiya et al.

[11] Patent Number: 4,556,997
[45] Date of Patent: Dec. 10, 1985

[54] APPARATUS FOR DRIVING MEDICAL APPLIANCES

[75] Inventors: Sanshiro Takamiya, Nagoya; Michisuke Yoshizawa, Tokyo; Akira Suzuki, Nishio, all of Japan

[73] Assignee: Aisin Seiki Kabushiki Kaisha, Kariya, Japan

[21] Appl. No.: 594,639

[22] Filed: Mar. 29, 1984

[30] Foreign Application Priority Data

Mar. 29, 1983 [JP] Japan ................................ 58-52853
Mar. 29, 1983 [JP] Japan ................................ 58-52854
Mar. 29, 1983 [JP] Japan ................................ 58-52855
Mar. 29, 1983 [JP] Japan ................................ 58-52856
Mar. 29, 1983 [JP] Japan ................................ 58-52857

[51] Int. Cl.⁴ ............................................. A61F 1/24
[52] U.S. Cl. ............................... 623/3; 280/289 WC; 128/1 D
[58] Field of Search ...................... 128/1 D, DIG. 3; 417/383, 389–390; 3/1, 1.2, 1.7; 280/289 WC

[56] References Cited

U.S. PATENT DOCUMENTS 4,046,137 9/1977 Curless et al. ..................... 128/1 D
4,162,543 7/1979 Shumakov et al. ............. 128/1 D X
4,431,206 2/1984 Pryor ............................ 280/289 WC Primary Examiner—Kyle L. Howell
Assistant Examiner—Francis J. Jaworski
Attorney, Agent, or Firm—Sughrue, Mion, Zinn, Macpeak & Seas

[57] ABSTRACT

A self-propelled wheelchair type artificial heart driving apparatus for giving freedom of movement to those patients who require an auxiliary artificial heart. Various safety devices are provided to avoid danger due to erroneous running of the wheelchair at the time when the patients board on or alight from the wheelchair and after alighting therefrom. For the purpose of enlarging a sphere of movement of the patients and preventing possible dangers, a motor-operated tube taking-up mechanism is provided and the wheelchair is permitted to run only when the tubes are in the orderly housed condition. A pressure compensating solenoid valve is provided in parallel to a pressure adjusting solenoid valve and a tank is dispensed with so as to make reduction in size of the artificial heart driving apparatus.

21 Claims, 39 Drawing Figures

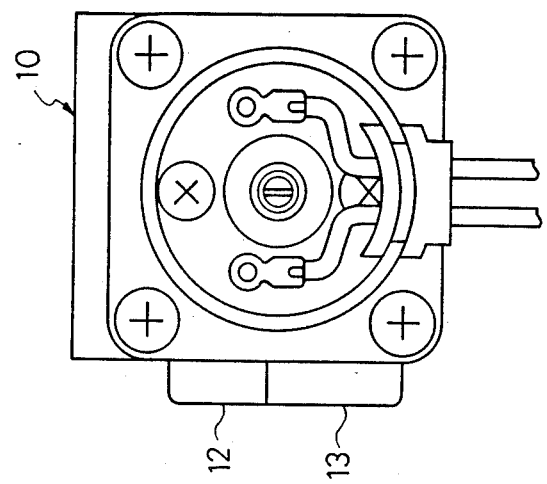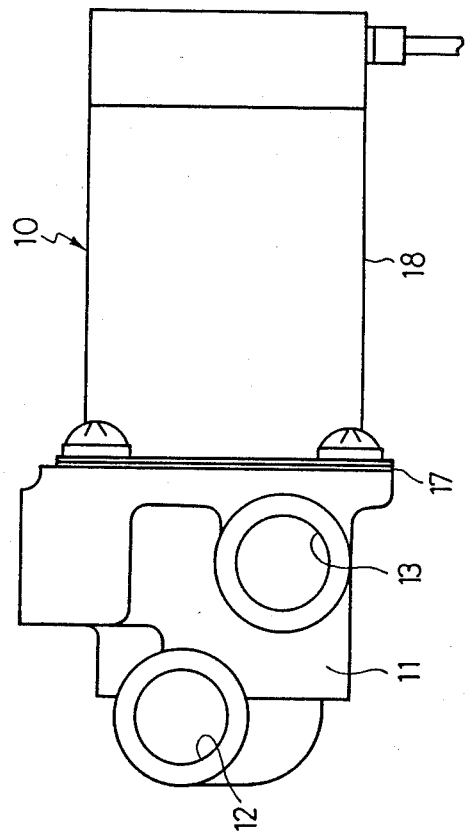

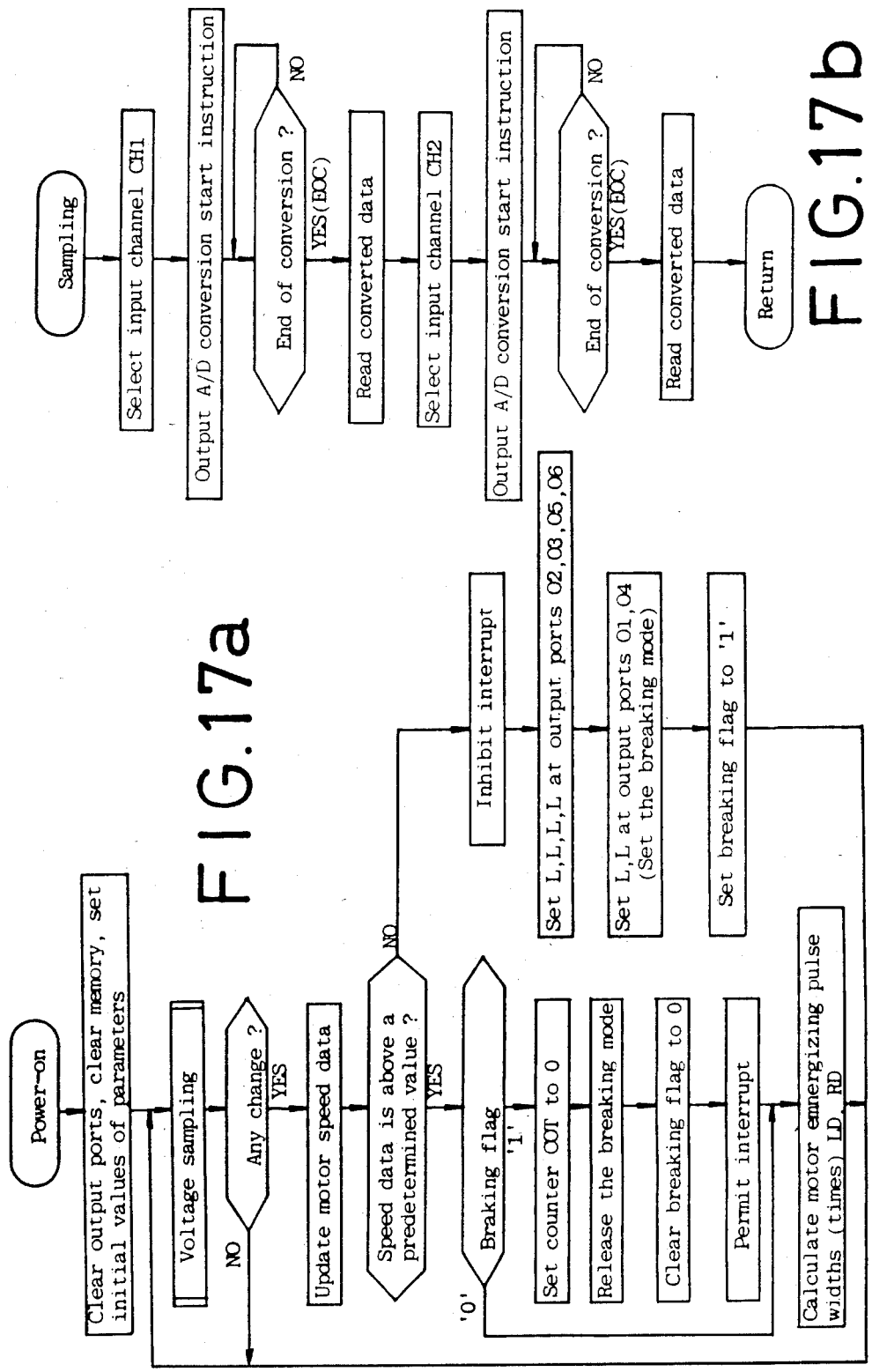

APPARATUS FOR DRIVING MEDICAL APPLIANCES

BACKGROUND OF THE INVENTION

The present invention relates to an apparatus for driving medical appliances, e.g., such as an artificial heart driving apparatus, and more particularly to an apparatus for driving medical appliances which can be self-propelled with a patient riding thereon.

It is usually impossible for some sick persons, particularly those with a serious illness who require, for example, an artificial heart (auxiliary heart), to move about because they have not the strength to walk and can not survive without a relatively large driving apparatus for the artificial heart being connected to their bodies. However, even such patients are relatively vigorous in many cases when the artificial heart (auxiliary heart) is operated satisfactorily, so it is not desirable to deprive such patients of their freedom of movement for a long period.

If an artificial heart driving apparatus can be mounted on an electric-powered wheelchair, this permits even those patients who carry an artificial heart on them to move about at any desired time. But an attempt to realize that will be accompanied by various dangers. For example, upon alighting from the wheelchair, if the wheelchair is erroneously moved after the patient has alighted therefrom, the patient will be exposed to danger because he is connected through tubes of a limited length to the artificial heart driving apparatus mounted on the wheelchair. In case of an electric-powered wheelchair, since the wheelchair, namely, artificial heart driving apparatus is readily moved by the simple operation of a lever or the like, the patient will get into serious danger if the control lever is accidentally caught by the hands, clothes, etc. of the patient when he is going to board on or alight from the wheelchair, or if the control lever is operated by mistake by those who are unfamiliar to the apparatus.

Further, when an artificial heart driving apparatus is mounted on an electric-powered wheelchair, tubes are preferably made longer which serve to connect between the artificial heart driving apparatus and an artificial heart, i.e., the patient, for the purpose of enlarging a sphere of movement of the patient. However, the longer tubes result in the danger that the tubes will be crushed under the patient's feet, the wheelchair itself, other moving equipment, etc. The fact that the tubes used in driving the artificial heart are crushed means a stoppage in functioning of the artificial heart. Since such patients are inclined to be weak in their physical strength in many cases, such stoppages are a serious influence on lives of the patients in the events not only if the tubes are broken, but also if the artificial heart is stopped even temporarily.

On the other hand, the artificial heart driving apparatus has a fairly large size because it requires a number of solenoid valves, tanks, pressure sources and other components, as described in, for example, the United Patent Application Ser. No. 480,181 (filed on Mar. 28, 1983). Accordingly, it is difficult to directly mount such large-sized apparatus into the vacant space of the electric-powered wheelchair with a small size.

SUMMARY OF THE INVENTION

It is a first object of the present invention to afford freedom of movement for those patients who need the aid of medical appliances such as an artificial heart (auxiliary heart) and who can remain relatively vigorous with such aid.

A second object of the present invention is to mount the medical appliance on a mobile unit such as an electric-powered wheelchair and to secure safety of the patients by preventing erroneous running of the mobile unit.

A third object of the present invention is to permit movement of the patients in a broader area with respect to the medical appliance driving apparatus by making longer tubes, etc. used to connect between the medical appliance and the patient, and to prevent stoppage of the medical appliance in its operation.

A fourth object of the present invention is to reduce the size of driving apparatus for the medical appliance and to mount such apparatus on a small sized mobile unit such as an electric-powered wheelchair.

To achieve the above first object, according to the present invention, a driving apparatus for the medical appliance is mounted on a mobile unit such as an electric-powered wheelchair.

To achieve the above second object, according to the present invention, at least one state of movable parts of the mobile unit and the medical appliance is detected and, in response to the detected result, the mobile unit is inhibited from moving in case that the patient does not wish to move and that there is a possibility of an anomaly to occur in the medical appliance. This is effected as follows in a preferred form of the present invention. Firstly, a control lever for controlling operation of the mobile unit is arranged detachably, and the mobile unit is inhibited from moving when the lever is detached. The lever can be operated simply, but it will be a danger to the patient when he boards or alights from the wheelchair, because of its sharply projected form. On the other hand, with the lever being arranged detachably, when it is removed by the patient himself or an attendant at the time of boarding or alighting, such projected lever disappears and danger can be avoided for the patient such as the mobile unit (medical appliance) being moved by mistake at the time of boarding or alighting and after alighting. Secondly, at least one armrest is provided on the mobile unit in such a movable fashion as it can be retracted, and the mobile unit is inhibited from moving when the armrest is in its retracted position. The presence of an armrest makes the patient more comfortable but, to the contrary, will be a very possible obstruction or danger to him at the time of boarding or alighting. Such obstruction or danger can be eliminated by having the armrest arranged in a retractable fashion. Also, by inhibiting movement of the mobile unit in the state when the armrest is in its retreated position, i.e., at the time of boarding or alighting and after alighting, it is impossible for the mobile unit to move unintentionally against a wish of the patient. Thirdly, the state of tubes or the like used to connect between the artificial heart, etc. and the apparatus for driving the same is detected, and the mobile unit is inhibited from moving when the tubes or the like are drawn out in a very long.

To achieve the above third object, according to the present invention, there is provided a take-up device for rolling the tubes or the like used to connect between the artificial heart, etc. and the apparatus for driving the same. This permits even long tubes to be housed in a retracted condition during boarding free of danger that they may be crushed flat so that a portion no longer than needed may be exposed to the outside, and to be drawn out a longer length when alighting. Thereby, it becomes possible to increase freedom of movement of the patient and to ensure safety of the medical appliance.

In the apparatus such as an artificial heart driving apparatus which is required to produce a predetermined pressure, it is preferably provided with a tank, i.e., an accumulator for maintaining the stable pressure even under the load. Particularly, in use for an artificial heart or the like which requires pressure changes having pulse-like sharp rises, a large-sized tank is generally employed in the driving apparatus so as to prevent reduction in the pressure. However, since such a tank has a large size, the conventional driving apparatus using the tank can not be directly arranged in the narrow space of the wheelchair in practice. On the other hand, when the tank is simply dispensed with, a solenoid valve for controlling the pressure must be increased in its size to compensate for the omission of the tank, with the result that the size of apparatus as a whole remains unchanged. According to the present invention, therefore, another solenoid valve is added in parallel to the conventional solenoid valve for adjusting the pressure, and it undergoes the opening and closing control in synchronous relation with a driving timing of the medical appliance such as an artificial heart, thereby to compensate for a temporary reduction of the pressure. This eliminates the need of a tank and permits the pressure control with a small-sized solenoid valve, thus achieving the above fourth object. In case of the artificial heart driving apparatus, there can be obtained a sufficient effect with the additional solenoid valves for compensating the pressure being provided not in the negative pressure system but in the positive pressure system only.

Other objects and features of the invention will become more apparent from a reading of the following description with reference to the drawings.

BRIEF DESCRIPTION OF THE DRAWINGS

FIG. 6b is a sectional view taken along the line VIb—VIb in FIG. 6a;

FIG. 7b is a perspective view showing the portion downwardly continued from the mechanism shown in FIG. 7a;

FIGS. 9a, 9b, 9c and 9d are a top plan, right side, left side and an enlarged longitudinal sectional view, respectively, for showing a solenoid valve used in the embodiment;

FIG. 12c is a timing chart showing operation of the circuitry of FIG. 12a;

FIGS. 17a, 17b and 17c are flow charts showing summary operation of a microcomputer unit CPU3;

DESCRIPTION OF PREFERRED EMBODIMENT

Figure 1:
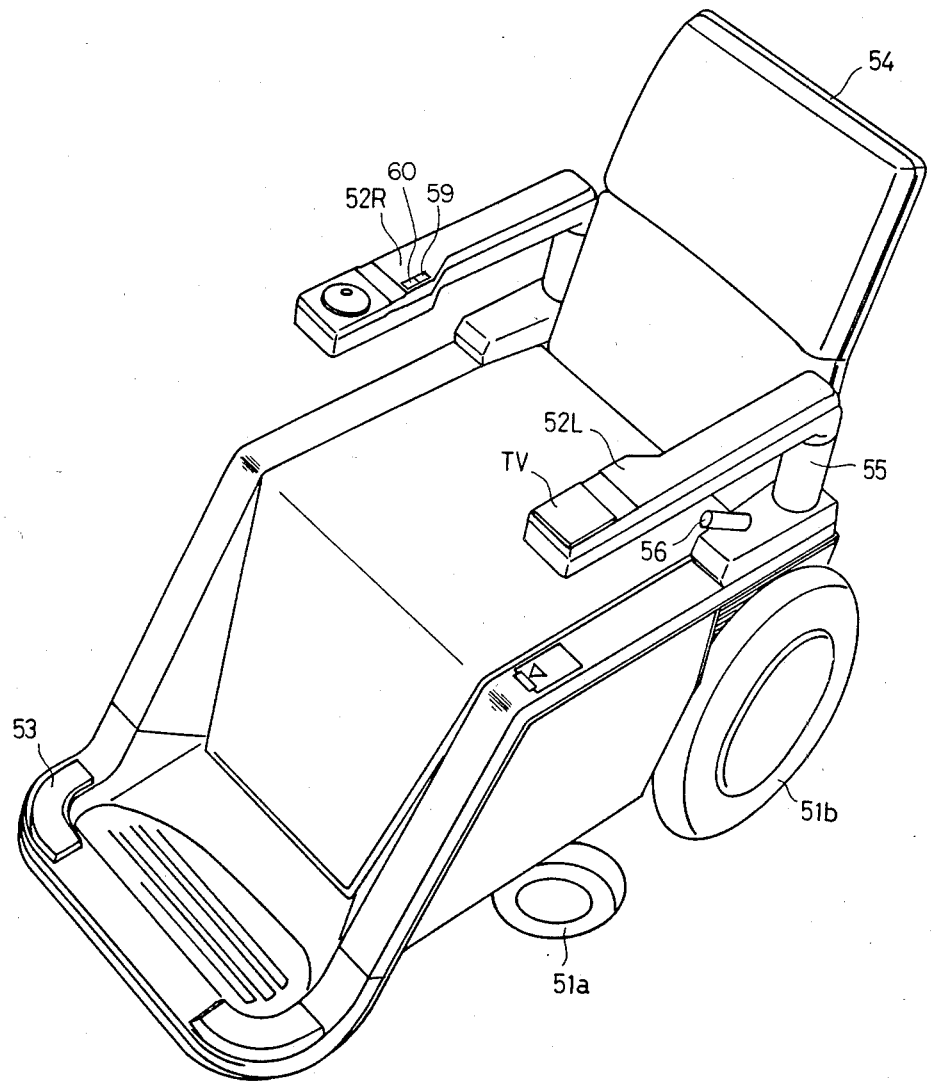
FIG. 1 is a perspective view showing the external appearance of an apparatus for embodying the present invention.
Figure 2A:
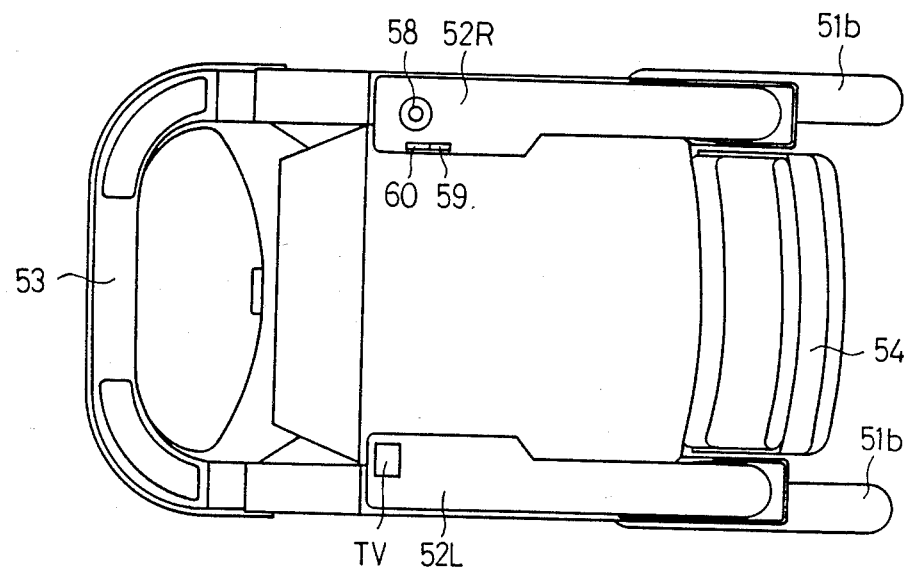
FIGS. 2a, 2b and 2c are a top plan, side and a front view of the apparatus of FIG. 1, respectively.
Figure 2C:
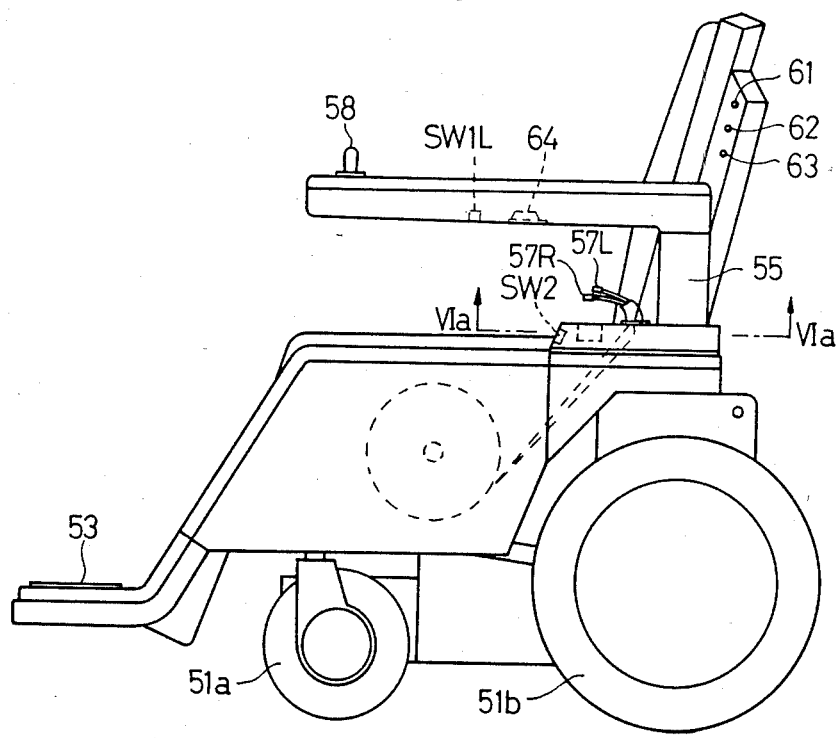
Figure 2B:
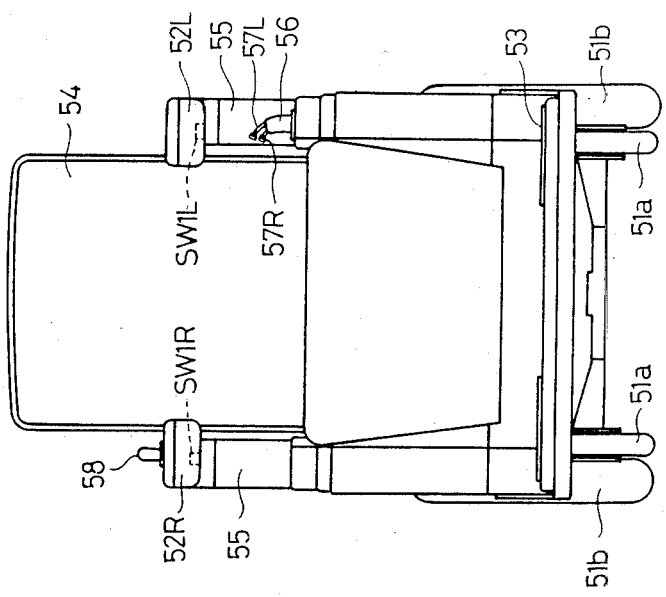

FIG. 1 shows a perspective view of an electric-powered wheelchair equipped with an artificial heart driving apparatus, and FIGS. 2a, and 2b and 2c are a top plan, side and a front view of the wheelchair of FIG. 1, respectively. Description will be made by referring to FIG. 1 and FIGS. 2a, 2b and 2c. The electric-powered wheelchair is provided with four wheels, front wheel 51a of which have a relatively small size and are arranged into the form of a caster. Rear wheels 51b have a relatively large size and are separately driven by independent motors through speed reduction mechanisms (not shown). There are provided armrests 52L and 52R on the left and right sides, respectively. Designated at 53 is a footrest and at 54 is a backrest.

Designated at 56 that appears near the root of a support shaft 55 for the lefthand armrest 52L is a cover of a port for taking out artificial heart driving tubes. When the patient is present on the wheelchair, artificial heart driving tube 57L and 57R are projected from the cover 56. To the leading end of each artificial heart driving tube is connected a connector, through which an artificial heart is connected to an artificial heart driving apparatus. Designated at TV located on the front end surface of the lefthand armrest 52L is a monitor television of small size. Designated at 58 projecting from the front end surface of the righthand armrest 52R is a control lever for running the wheelchair. As described later, this control lever 58 is detachable so that such a large projected lever will be removed from the surface of the armrest 52R when it is taken out, as will be seen from FIG. 1.

Further, as described later, the armrests 52L and 52R are turnable horizontally (counterclockwise for 52L, clockwise for 52R) about the support shafts 55 by 90 degrees, respectively. Switches SW1L and SW1R provided in the lower sides of the armrests 52L and 52R, respectively, provide instructions for releasing the locked state of the arm rests. Designated at 59 is an alarm display of the artificial heart driving apparatus, and at 60 is an alarm display of the electric-powered wheelchair. Each of those alarm displays includes therein two light emitting diodes, one of which indicates the green color in the normal condition and the other of which indicates the red color in the event any anomaly occurs. Designated at SW2 is a take-up instruction switch for a motor-operated tube taking-up mechanism and, when the switch is operated, the artificial heart driving tubes 57L and 57R are rolled into the interior of the wheelchair. Designated at 61 is a key switch for the artificial heart, at 62 is a connector for electrical connection of a control board for setting and instructing various control parameters of the artificial heart driving apparatus, and at 63 is a connector for electrical connection of an external monitor television similar to the monitor television TV on the armrest. At 64 is an alarm buzzer which issues an alarm in the event of an anomaly.

Figure 3A:
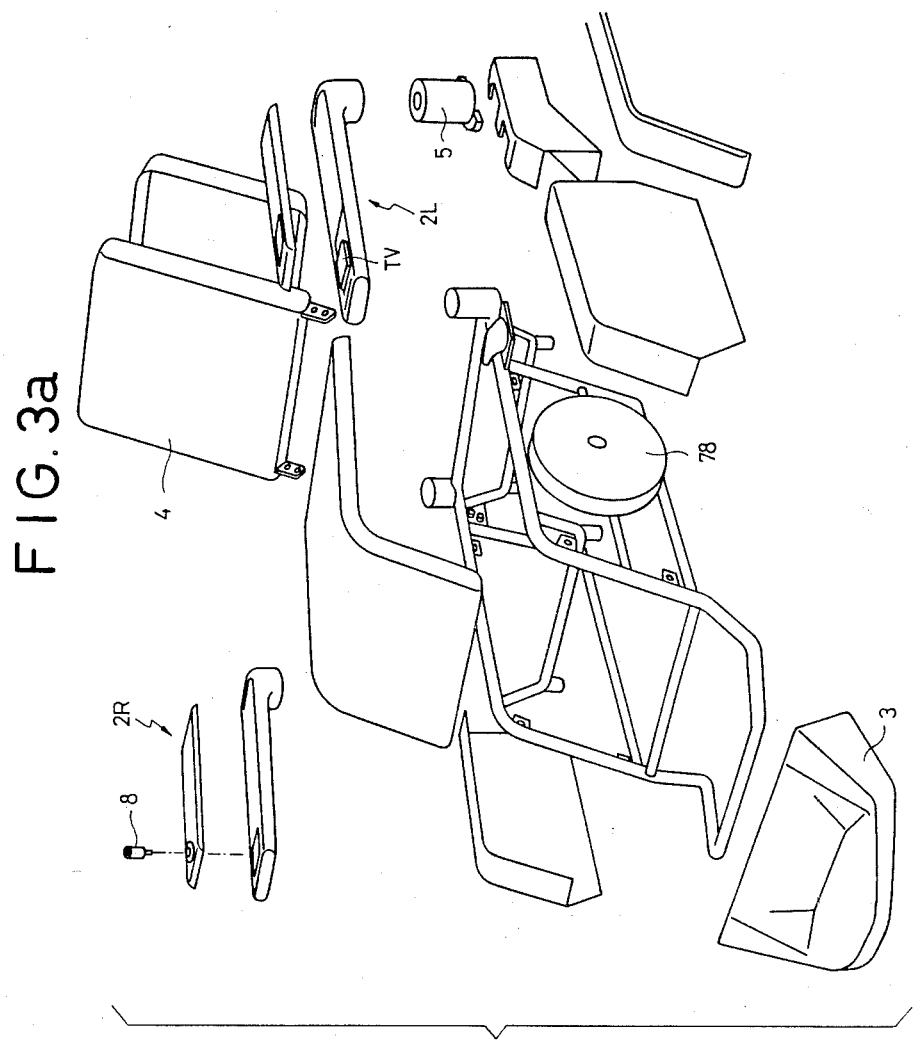
FIGS. 3a and 3b are schematic exploded perspective views of the apparatus of FIG. 1.
Figure 3B:
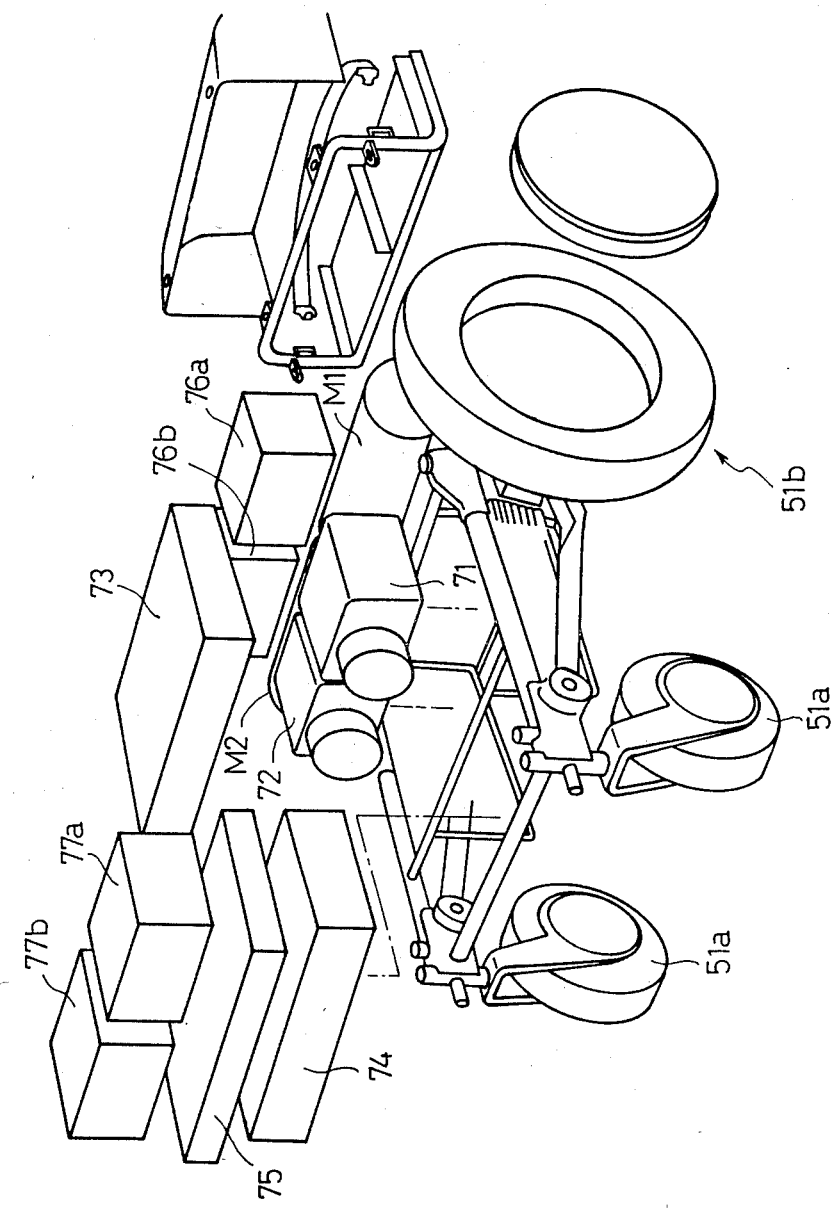

FIGS. 3a and 3b show exploded perspective views of the wheelchair of FIG. 1. It is to be noted that minor parts are omitted in these figures. FIG. 3a mainly illustrates a housing of the wheelchair, and FIG. 3b illustrates a chassis of the wheelchair and principal components of the artificial heart driving apparatus. Those principal components of the artificial heart driving apparatus and the electric-powered wheelchair will be now described by referring to FIGS. 3a and 3b.

Designated at 71 is a vacuum pump, at 72 is a compressor, at 73 is a valve unit, at 74 is a muffler (sound arrester), at 75 is a wheelchair driving motor control unit, at 76a and 76b are batteries for the artificial heart driving apparatus, and at 77a and 77b are batteries for the wheelchair. At M1 and M2 are motors for driving the righthand rear wheel and the lefthand rear wheel, respectively. These motors are of direct current motors. At 78 is a drum for rolling the artificial heart driving tubes therearound.

Figure 4:
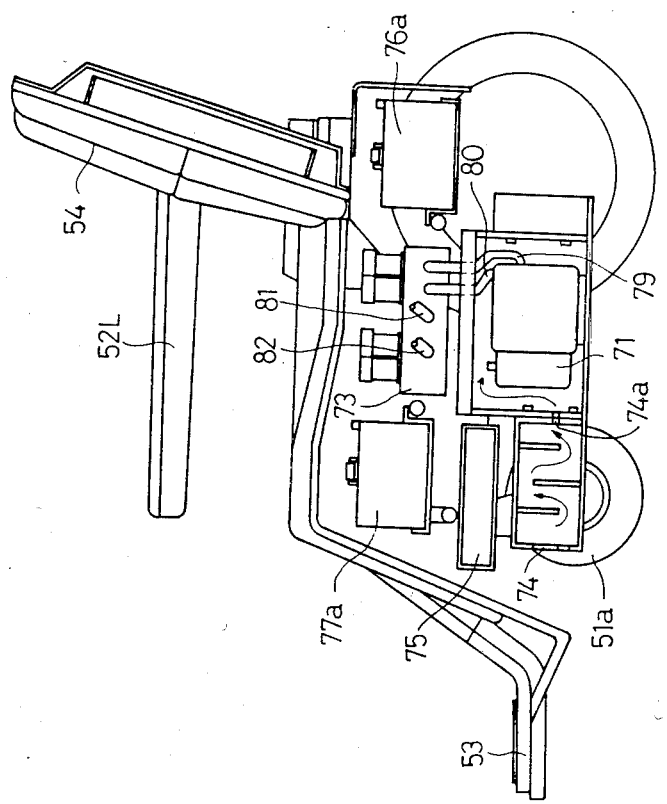
FIG. 4 is a side view showing the internal structure of the apparatus of FIG. 1.

FIG. 4 shows a section of the wheelchair equipped with the artificial heart driving apparatus. Referring now to FIG. 4, the compressor 71 and the vacuum pump 72 are placed in an enclosure for prevention of noise and communicated with the atmosphere through the muffler 74. Both side members and an upper member of the enclosure housing therein the compressor 71 and the vacuum pump 72 are formed of rubber. Since the temperature in an internal space of the enclosure is increased due to heat generated by the compressor 71 and the vacuum pump 72, the fluid inflow side of the compressor 71 is exposed to the internal space in this embodiment, so that air of low temperature led from a hole 74a of the muffler 74 may be circulated within the space. The vacuum pump 72 is connected to the muffler 74 through a pipe (not shown). Pressure output terminals of the compressor 71 and the vacuum pump 72 are connected to the valve unit 73 through pipes 79 and 80, respectively. Designated at 81 and 82 are pressure output terminals for the artificial heart driving apparatus of two systesm. In this embodiment, all of electronical control devices except for the wheelchair driving motor control unit 75 is mounted in the interior (rear side) of the backrest 54.

Figure 5A:
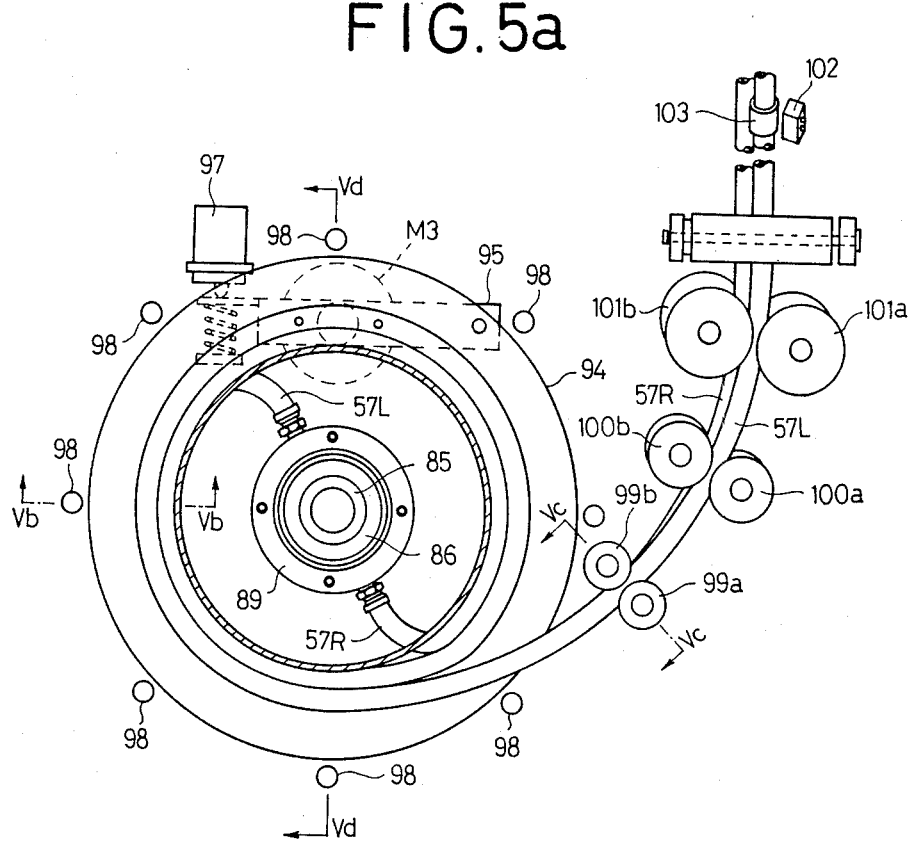
FIGS. 5a, 5b, 5c, 5d and 5e are a sectional view taken along the line Va—Va in FIG. 5d, sectional view taken along the line Vb—Vb in FIG. 5a, sectional view taken along the line Vc—Vc in FIG. 5a, sectional view taken along the line Vd—Vd in FIG. 5a and a sectional view taken along the line Ve—Ve in FIG. 5d, respectively, for showing a tube taking-up mechanism 78.
Figure 5B:
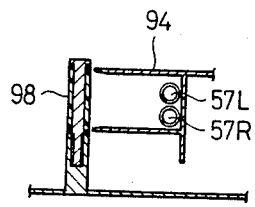
Figure 5C:
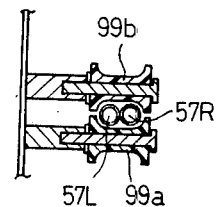
Figure 5D:
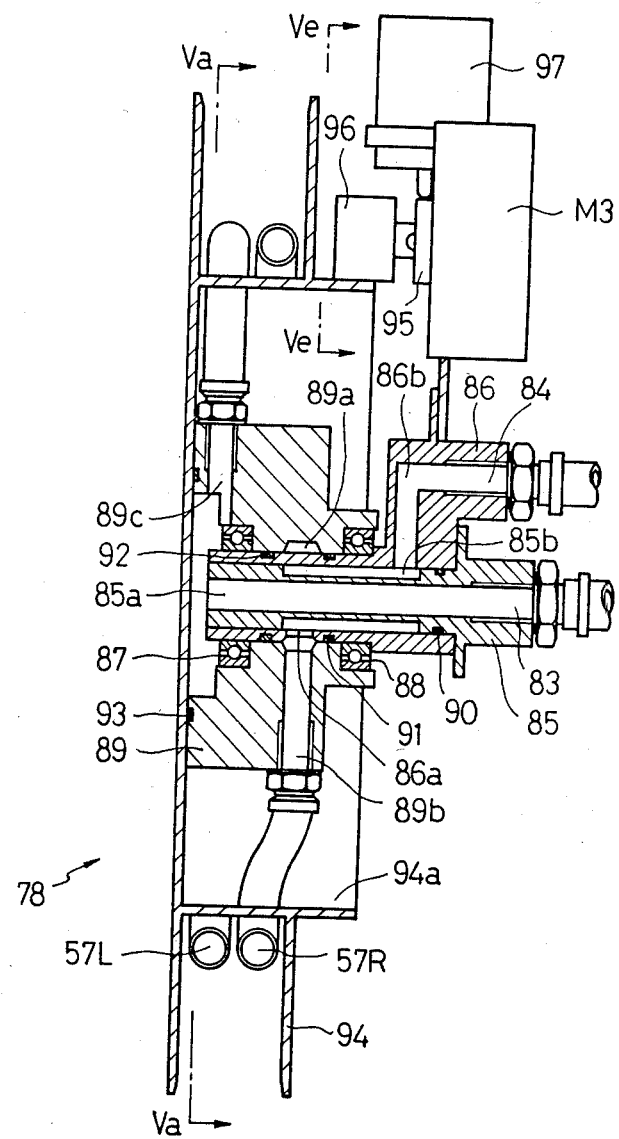

The construction in the vicinity of the drum 78 is shown in FIGS. 5a, 5b, 5c, 5d and 5e. Referring first to FIG. 5d, to openings 83 and 84 are connected pipes led from the pressure output terminals 81 and 82 of the artificial heart driving apparatus, respectively. A first member 85 has a cylindrical form and is formed with a bore 85a axially penetrating therethrough and with a groove 85b in its peripheral surface. A second member 86 has a cylindrical form except for the part near the opening, and it is fitted to the outer periphery of the first member 85 in such a manner that holes 86a and 86b, the latter communicating with the opening 84, are located opposite to the groove 85b. A third member 89 is rotatably fitted to the outer periphery of the second member 86 through bearings 87 and 88. The third member 89 is formed with a groove 89a surrounding the periphery of the second member 86 at a position opposite to the groove 85b of the first member and the hole 86a of the second member, and with a bore 89b communicating with the groove 89a. The third member 89 is also formed with a bore 89c communicating with the bore 85a of the first member.

A tube reel 94 is connected to the third member 89. One ends of the artificial heart driving tubes 57R and 57L are connected to the bores 89b and 89c of the third member as pressure output terminals, respectively, and the driving tubes extending from those terminals are exposed to the outside while being rolled along the peripheral surface of the tube reel 94. Incidentally, designated at 90, 91, 92 and 93 are seal rings.

Figure 5E:
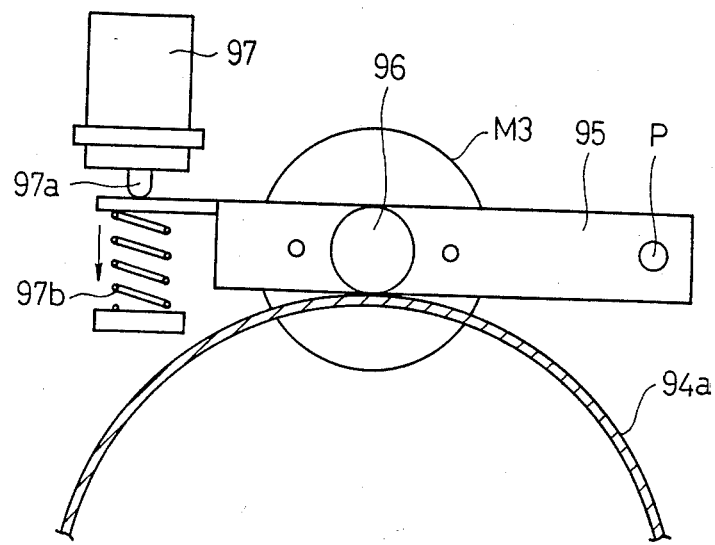

Referring now also to FIG. 5e, designated at M3 is a motor for taking-up the tubes and formed of a stepping motor in this embodiment. The motor M3 is fixed to a plate-like support member 95 and provided on its driving shaft with a reel driving roller 96. The support member 95 has one end rotatably supported at a point P and the other end supported by a plunger 97a of an electromagnetic actuator 97.

The support member 95 is normally lifted upwards by the force of a compression coil spring 97b, but when a solenoid of the electromagnetic actuator 97 is energized, the support member 95 is pushed downwards by the actuator, thus causing the reel driving roller 96 to be pressed against a peripheral surface 94a of the tube reel.

Description will be now made by referring to FIGS. 5a, 5b and 5c. On the outer side of the tube reel 94, there are arranged eight rotatable Teflon-made rollers 98 along the peripheral surface thereof to prevent the artificial heart driving tubes 57R and 57L from slipping away from the tube reel 94. The pair of (two) artificial heart driving tubes 57R and 57L led from the tube reel 94 are extended through a tube passage which is formed by three parts of rotatable Teflon-made rollers 99a-99b, 100a-100b and 101a-101b each recessed at the central part, in order that the tubes will not be got entangled or caught within the housing.

In this embodiment, the artificial heart driving tubes are guided in such a way as those roller pairs are arranged to follow an inclined curve and the size of the rollers is increased with their positions being more spaced from the reel. A proximity switch (sensor) 102 for detecting magnetism is provided near the passage of the artificial heart driving tubes 57L, 57R, and the artificial heart driving tube 57L is provided with an iron piece 103 at the part which locates opposite to the proximity switch 102 when the tube is completely taken up.

Figure 6A:
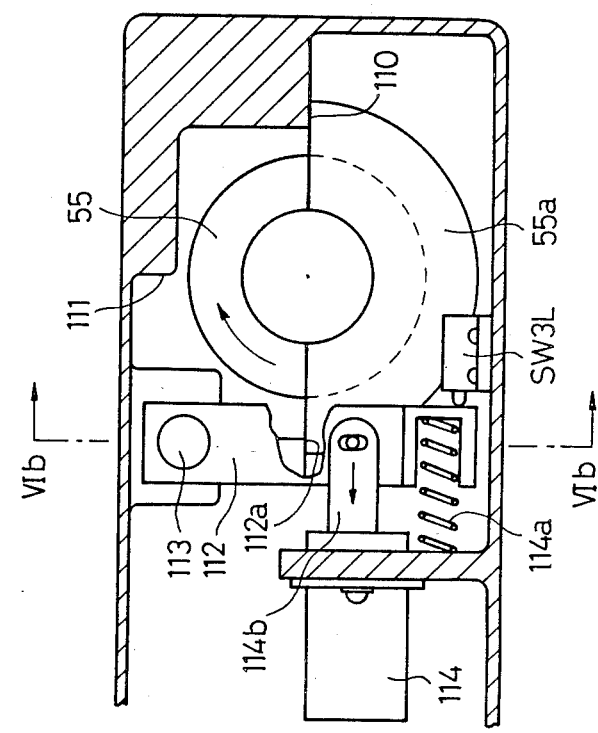
FIG. 6a is a sectional view taken along the line VIa—VIa in FIG. 2c.
Figure 6B:
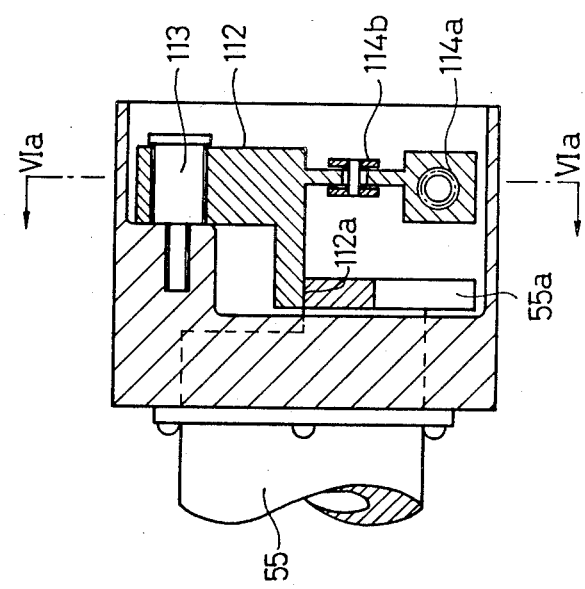

FIG. 6a shows the support structure of the armrest supporting shaft 55, etc, when viewed from the line VIa—VIa in FIG. 6b and FIG. 2c, and FIG. 6b shows a section when viewed from the line VIb—VIb in FIG.

6a. Referring now to FIGS. 6a and 6b, the support shaft 55 has a cylindrical form and is provided with a semi-circular flange 55a at its lower part. A rotation of the support shaft 55 in one direction is restricted by that one end of the flange 55a strikes against a projected part 110 on the housing side, and a rotation thereof in the other direction is restricted by the presence of a projected part 111 on the housing side or a projected part 112a of an arm 112.

The arm 112 has one end rotatably supported by a pin 113 and the other end supported by an electromagnetic actuator 114. The arm 112 is normally pushed toward the side of the support shaft 55 by a spring 114a and, in this state as shown in FIG. 6a, the flange 55a is locked by the projected part 110 of the housing and the projected part 112a of the arm.

When a solenoid of the electromagnetic actuator 114 is energized, a plunger 114b is retracted and the arm 112 is turned clockwise, thus causing the projected part 112a to be released from the flange 55a. As a result, the support shaft 55 is released from its locked state. In this condition, a movement of the flange 55a is restricted by the projected parts 110 and 111 of the housing, so that the support shaft, i.e., the armrest 52L becomes rotatable with a turning angle in a range up to 90 degrees.

Further, a microswitch SW3L for detecting a position of the arm 112 is provided near one end of the arm 112 (another microswitch SW3R is provided on the side of the other armrest). The switch is turned ON in the locked state of the armrest as shown in FIG. 6a, and turned OFF in the unlocked state thereof. Incidentally, cords, etc. used for connecting the switches and others on the armrest to the apparatus body are wired through the internal bore of the support shaft 55.

Figure 7A:
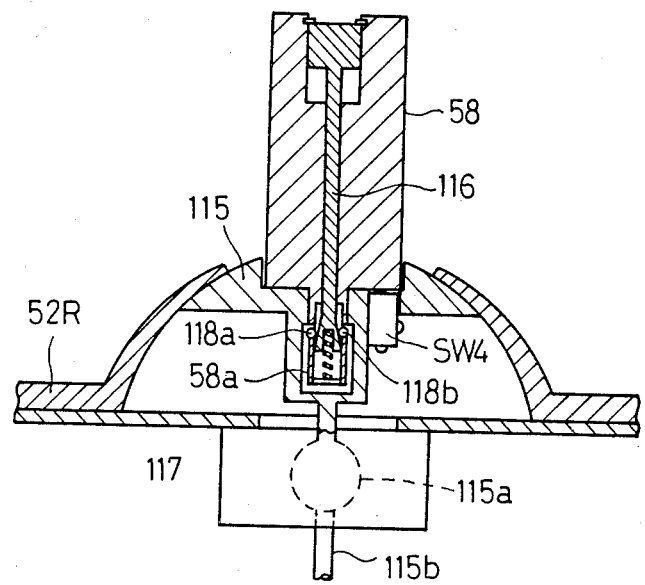
FIG. 7a is a sectional view showing the vicinity of a running control lever 58.

The vicinity of the control lever 58 is shown in FIG. 7a. A lower end 58a of the control lever has a smaller diameter, and this end is fitted into the recess of a lower support mount 115. The control lever 58 is formed with a bore axially penetrating through the center thereof except for a part of the end 58a, and a rod 116 is inserted through the bore. A compression spring 117 is disposed on the lower side of the bulged portion of the rod 116 at its lower end, while minute balls 118a and 118b are disposed on the upper side thereof. The control lever end 58a is formed at positions adjacent to the minute balls 118a and 118b with holes having a diameter slightly smaller than that of the minute balls 118a, 118b.

In the state as shown in FIG. 7a, therefore, the rod 116 is pushed upwards by the force of the spring 117 to push the minute balls 118a and 118b also upwards, whereby the minute balls 118a and 118b are slightly projected to the outer side of the control lever 58 through the aforesaid holes. On this occasion, an outer diameter of the control lever end 58a including the minute balls is selected to be greater than an inner diameter of the upper recess of the support mount 115. Thus, the control lever 58 is locked in this stage and it can not be removed out even with a pulling-up force being applied thereto.

On the other hand, when a force pushing down the rod 116 is applied to the control lever 58 from above, the force pushing the minute balls 118a and 118b toward the outer side is offset so that the minute balls are apart from the holes of the control lever end 58a, thus causing the control lever to be unlocked. As a result, the control lever 58 can be pulled out easily. The support mount 115 is provided with a microswitch SW4 for detecting the presence of the control lever 58. The contact of the switch SW4 is turned ON when the control lever 58 is fitted as shown in FIG. 7a, and turned OFF when it is pulled out.

The support mount 115 is supported at a lower spherical portion 115a thereof so as to be freely rotatable about the portion 115a. A long rod 115b is extended downwards from the spherical portion and has its lower end arranged as shown in FIG. 7b.

Figure 7B:
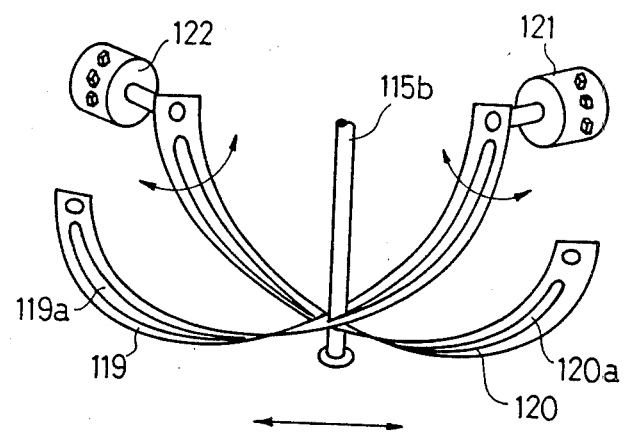
Figure 9D:
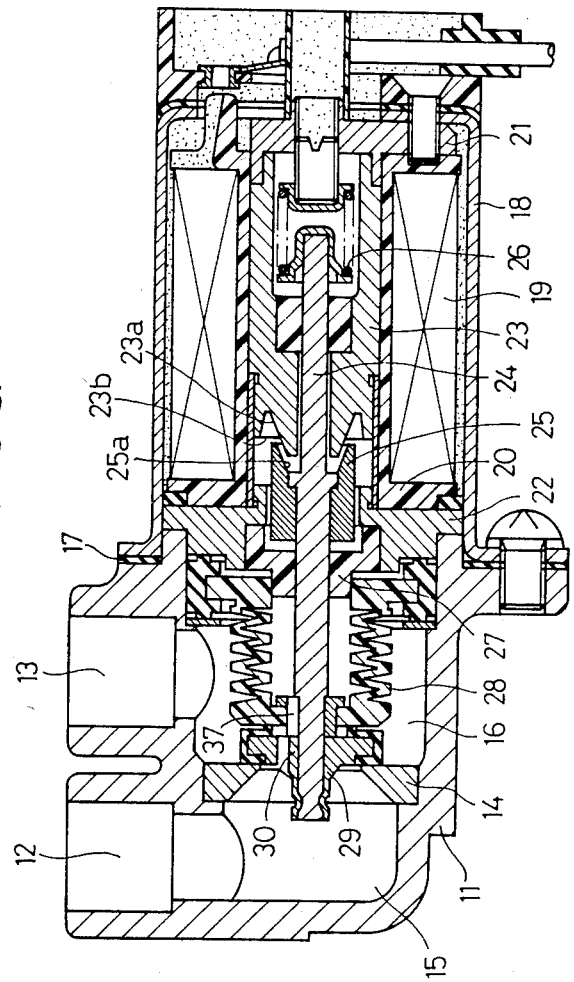
Figure 9C:
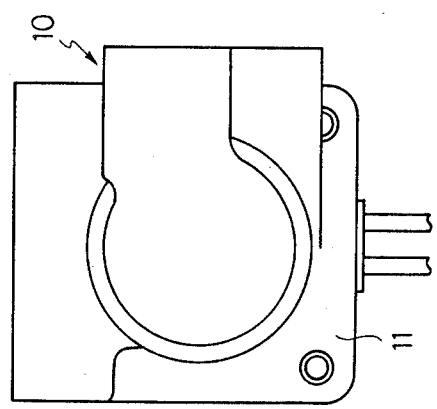

Referring now FIG. 7b, a pair of semi-circular thin plates 119 and 120 are superimposed at a right angle to each other. The plates 119 and 120 are formed with continuous elongated slots 119a and 120a, respectively, and the rod 115b is inserted through the crossed part of both slots 119a and 120a. The plates 119 and 120 are rotatably supported at their both ends. The plate 119 has one end connected to a rotary shaft of a variable resistor 121, and the plate 120 has one end connected to a rotary shaft of a variable resistor 122.

Figure 8:
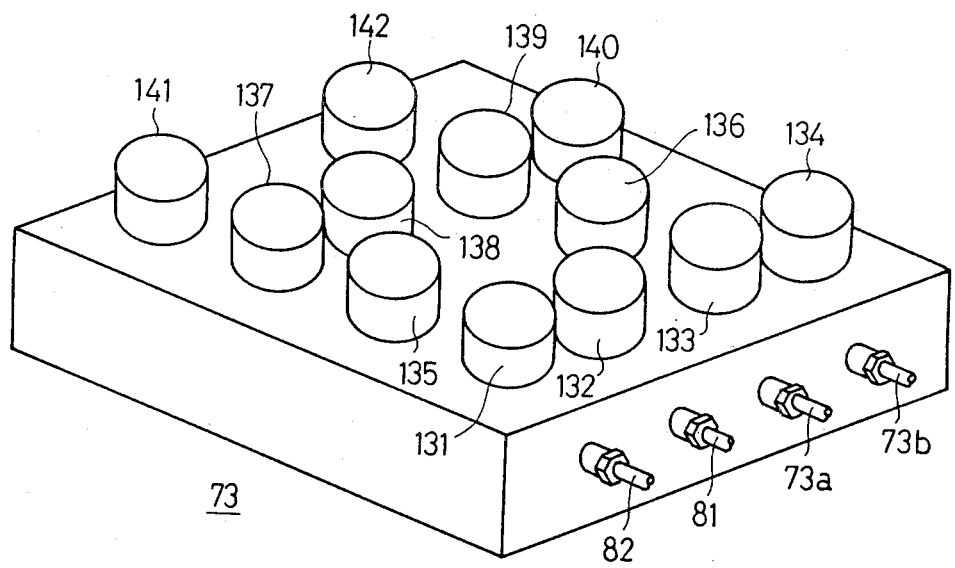
FIG. 8 is a perspective view showing a valve unit 73 in FIG. 3b.

The external appearance of the valve unit 73 is shown in FIG. 8. Referring now to FIG. 8, the valve unit 73 includes a number of solenoid valves and pressure sensors. Many bores for fluid connections of passages are formed in the interior of a box-like casing, thereby to eliminate of the need of pipes used to connect the passages for the individual solenoid valves. In this embodiment, there are employed twelve solenoids of the same construction. Though not shown in FIG. 8, there are employed four pressure sensors. Designated at 73a is a negative pressure intake port, at 73b is a positive pressure intake part, and at 81, 82 are pressure output terminals of the independent systems, respectively. The pipes connected to those output terminals are in turn connected to the openings 83 and 84 of the tube taking-up mechanism.

Further, the valve unit 73 is provided at the not shown part thereof with other output terminals for releasing the pressures from the same systems as 81 and 82, respectively. The pipes connected to those of other output terminals are in turn directly connected to air tube connector 123 for emergency shown in FIG. 2c while bypassing the tube taking-up mechanism. This connector is used in the event there occurs any anomaly in the artificial heart driving tube 57L or 57R, and the output terminals of the connector are normally closed.

FIGS. 9a, 9b, 9c and 9d show a top plan, right side, left side and an enlarged longitudinal sectional view of each solenoid valve (electromagnetic control valve) shown in FIG. 8, respectively. Referring now to FIGS. 9a, 9b, 9c and 9d, the solenoid valve has a valve housing 11 formed with a first port 12 and a second port 13. An internal space of the housing 11 is divided by a valve seat 14 into a first internal chamber 15 in communication with the first port 12 and a second internal chamber 16 in communication with the second port 13. A coil case 18 of magnetic material is fixed to the valve housing 11 via a sealing material 17.

Within the case 18 is inserted a coil bobbin 20 having a coil 19 wound therearound, the coil bobbin 20 being supported by a pair of magnetic material bases 21, 22. A fixed core 23 of magnetic material is secured to the base 21. The core 23 has a central hollow space and a guide rod 24 is non-magnetic material is extended to penetrate therethrough. A movable core 25 of magnetic material is fixed to the rod 24. One end of the rod 24 is pushed leftwards by a coil spring 26. The other end of the rod 24 penetrates through a bearing 27 and a bellows 28, and it has its extreme end part to which is fixed a valve body 29. An internal space of the bellows 28 is communicated with the first internal chamber 15 (in the state illustrated) or with the second internal chamber 16 (when the rod 24 is driven rightwards) through small holes 30 and 37.

When the coil 19 is energized, there causes magnetic flux circulating through the core 23-core 25-base 22-case 18-base 21-core 23 and a force for attracting the core 25 to the core 23 acts on the former, whereby the rod 24 is moved rightwards up to a point where this attraction force is balanced by the repulsion force of the coil spring 26. As a result, the valve body 29 is apart away from the valve seat 14 by a distance in accordance with the attraction force. An end face 23c of the core 23 has the W-like form, while an end face 25a of the core 25 has the recessed form receiving the central projection of the opposite end face 23a. Further, inner side faces 23b of both end projections in the W-like form are tapered. By the presence of such tapers, the ratio of a energization level to a movement amount of the rod 24 (i.e., a gap between 23a and 25a) is made to have the proportional relationship in a wider range. Also, the solenoid valve of this kind has good responsivity of its movable part and permits the high-speed opening and closing control.

Figure 10:
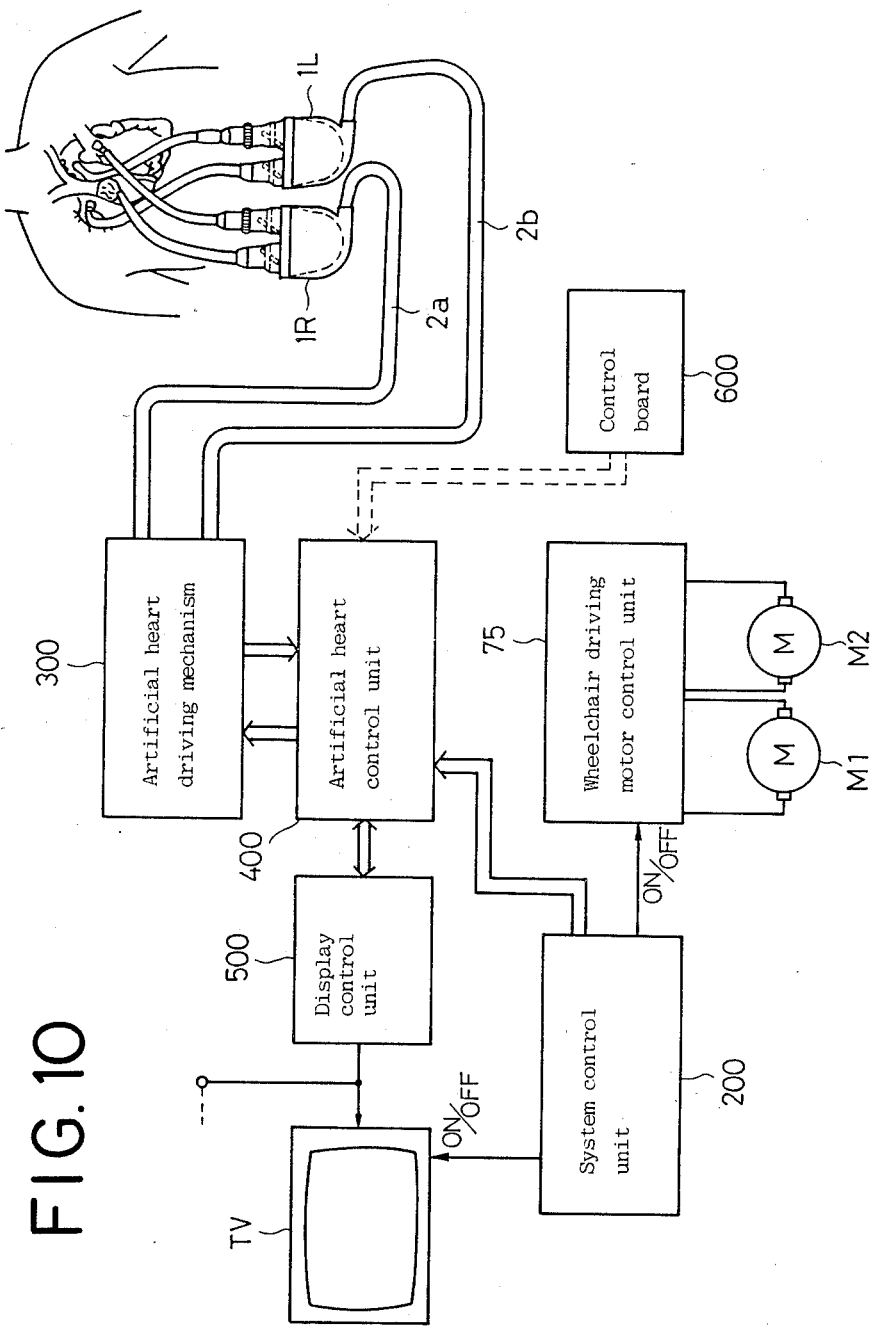
FIG. 10 is a block diagram showing the schematic system configuration of the apparatus of FIG. 1.

FIG. 10 shows the schematic operational configuration of the entire apparatus of FIG. 1. Referring now to FIG. 10, designated at 1R and 1L are artificial hearts. When predetermined positive and negative pressures are alternately applied to these artificial hearts 1R, 1L, a diaphragm placed therein is pulsated to feed blood in a certain direction determined by actions of valves. Tubes 2a and 2b used for applying pressures to the artificial hearts 1R and 1L are connected to the artificial heart driving tubes 57R and 57L, respectively, through connectors fitted to the ends thereof.

An artificial heart driving mechanism 300 for applying the air of predetermined pressure to the artificial heart 1R and 1L is electrically controlled by an artificial heart control unit 400. A display control unit 500 generates a composite video signal for indicating informations issued from the artificial heart control unit 400 on the monitor television TV. The display control unit 500 may be formed of a commercially available unit comprising a display signal memory, character generator (ROM), integrated circuits for display control, etc. A control board 600 is a switch board for changing and instructing various artificial heart driving parameters, and it is connectable to the artificial heart control unit 400. It is to be noted that the optimum values are previously set in a read-only memory (ROM) within the artificial heart control unit 400 as the driving parameters, and that there is practically no possibility to use the switch board.

The wheelchair driving motor control unit 75 serves to control the direct current motors M1 and M2 operatively coupled to the pair of rear wheels 51b of the wheelchair. A system control unit 200 reads the states of various switches, sends a signal to the artificial heart control unit 400 and controls turning ON/OFF of the wheelchair driving motor control unit 75, turning ON/OFF of the monitor television TV, etc.

Figure 11:
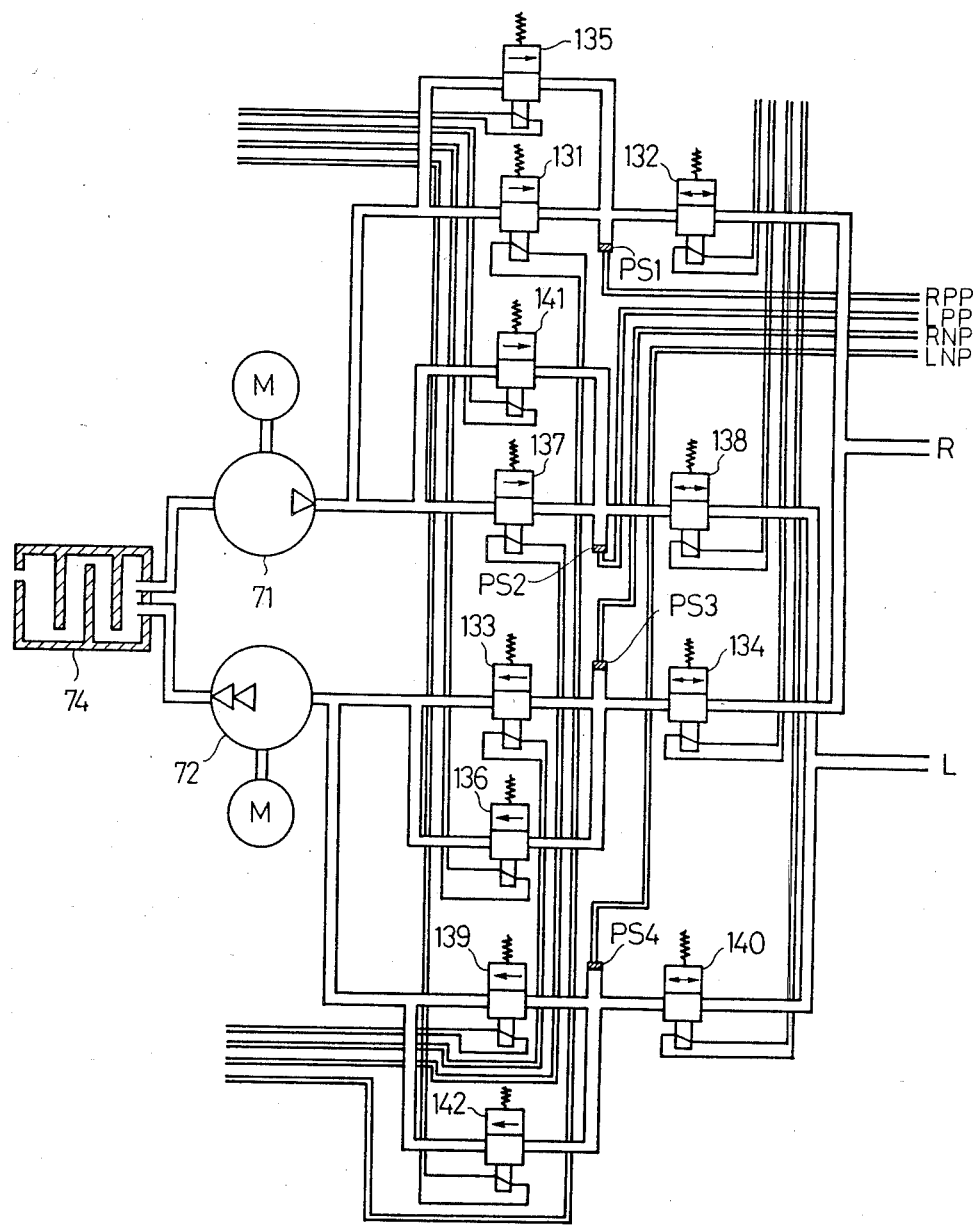
FIG. 11 is a block diagram showing an artificial heart driving mechanism 300 in FIG. 10.

The detailed of the artificial heart driving mechanism 300 in FIG. 10 is shown in FIG. 11. Referring now to FIG. 11, the compressor 71 and the vacuum pump 72 are communicated with the atmosphere through the muffler 74. A number of solenoid valves, etc. are connected to the pressure output terminals of the compressor 71 and the vacuum pump 72, those constituent parts being grouped into two systems. One system serves to drive the righthand artificial heart 1R, while the other system serves to drive the lefthand artificial heart 1L.

The righthand system will be first described. Designated at 131 is a pressure adjusting valve for adjusting the positive pressure to be applied to the artificial heart, the valve being controlled in its opening and closing operation in response to output from a pressure sensor PS1 dropped in the output terminal passage thereof. Designated at 132 is a solenoid valve which serves to make the ON/OFF control for application of the predetermined positive pressure obtained by the pressure adjusting valve 131, etc. to the artificial heart 1R. A solenoid valve 135 connected in parallel to the pressure adjusting valve 131 is provided to compensate reduction in the pressure which occurs at the rising of the pressure applied to the artificial heart. Similarly, a solenoid valve 133 adjusts the negative pressure, a solenoid valve 134 makes the ON/OFF control of the negative pressure applied to the artificial heart, and a solenoid valve 136 compensates reduction in the pressure. A pressure sensor PS3 detects the negative pressure in this system. The lefthand system is constructed in a similar way. That is, solenoid valves 137, 138 and 141 are a pressure adjusting valve, a pressure ON/OFF valve and a pressure compensating valve for the positive pressure system, respectively, and solenoid valves 139, 140 and 142 are a pressure adjusting valve, a pressure ON/OFF valve and a pressure compensating valve for the negative pressure system, respectively. Pressure sensors PS2 and PS4 serve to detect the pressures in the positive and negative pressure systems, respectively.

Figure 12A:
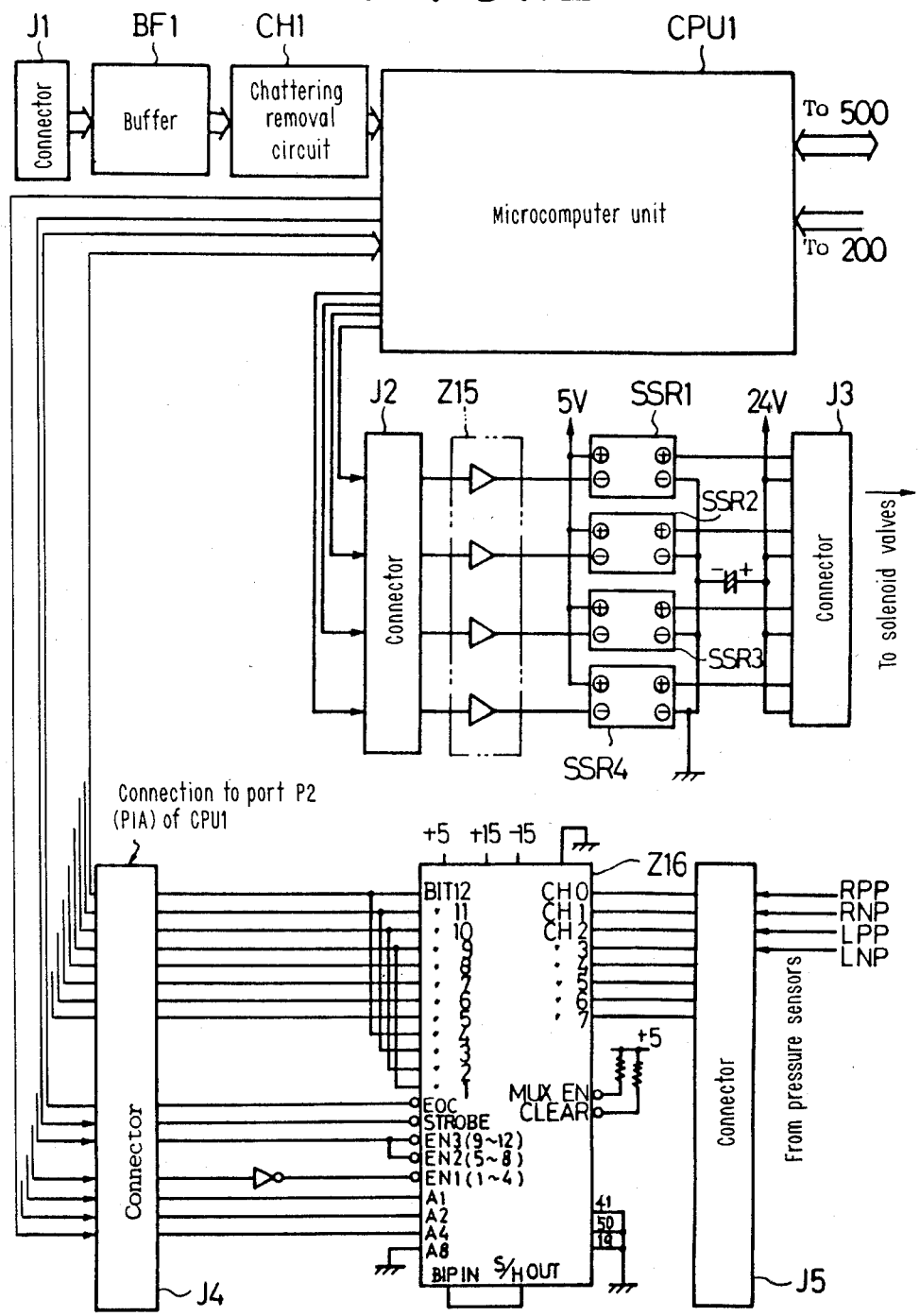
FIGS. 12a and 12b are block diagrams of an artificial heart control unit 400 in FIG. 10.
Figure 12B:
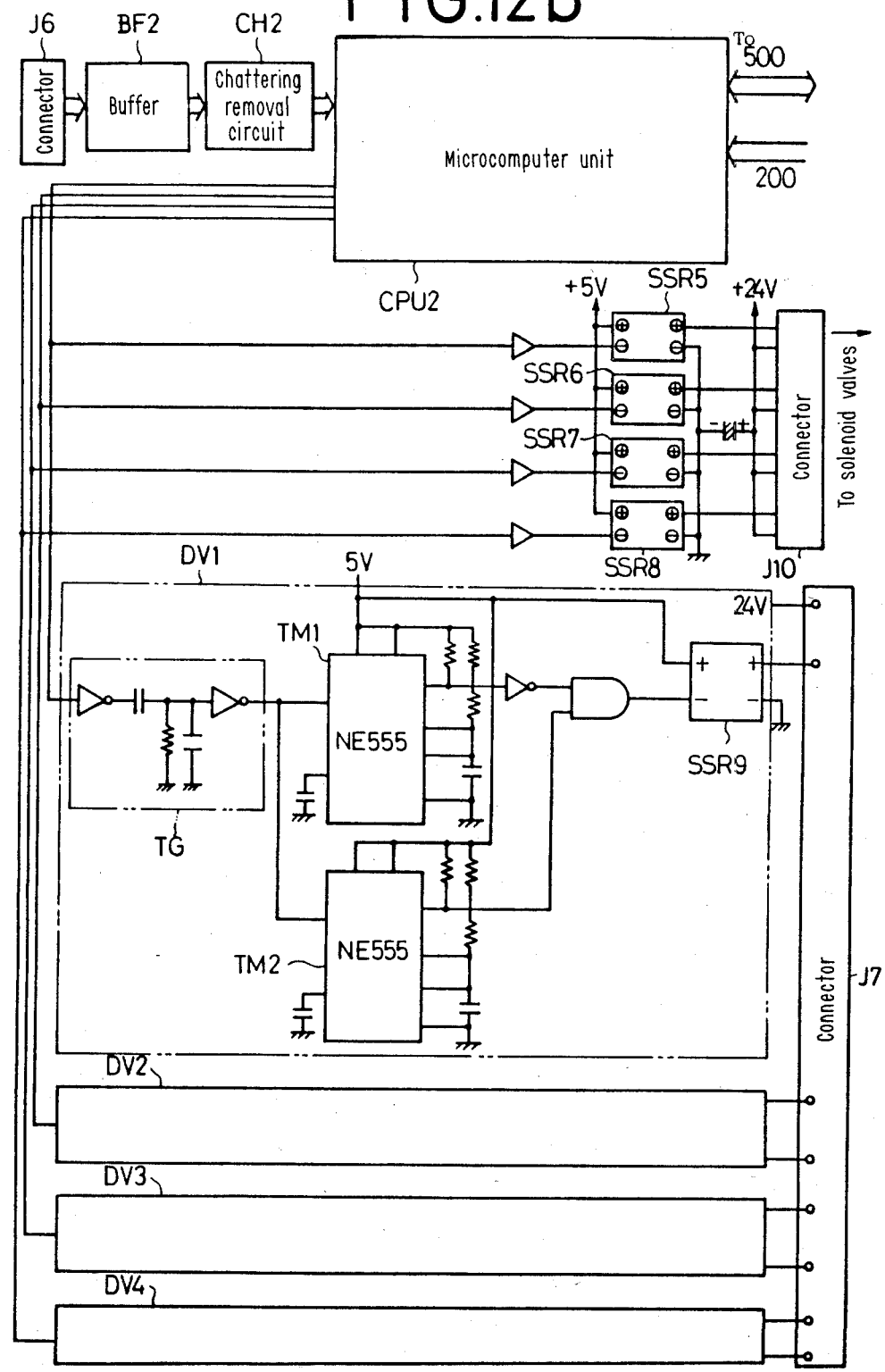

The configuration of the artificial heart control unit 400 in FIG. 10 is shown in FIGS. 12a and 12b. Referring first to FIG. 12a, this circuitry performs the pressure adjusting control. More specifically, it controls opening and closing of the solenoid valves 131, 137, 133 and 139 in accordance with both signals from the pressure sensors PS1, PS2, PS3 and PS4 and the preset pressure values. This circuitry itself is controlled by a microcomputer unit CPU1.

Analog signals RPP, LPP, RNP and LNP from the pressure sensors PS1, PS2, PS3 and PS4 are applied to an analog/digital converter Z16 through a connector J5. The A/D converter Z16 is provided with eight input channels and has resolution of 12 bits. Designated at EOC is an output terminal for a signal for indicating the completion of conversion, at STROBE is an input terminal for giving the instruction of conversion, at EN1, EN2 and EN3 are input terminals for controlling output allowance/prohibition of the converted digital data, and at A1, A2, A4 and A8 are input terminals for specifying input channels. The A/D converter Z16 is connected to the microcomputer CPU1 through a connector J4.

Solenoids of the pressure adjusting solenoid valves 131, 137, 133 and 139 are connected to a connector J3. Designated at SSR1, SSR2, SSR3 and SSR4 are solid state relays for making the ON/OFF control of energization for those solenoids, which relays are controlled by output ports of the microcomputer unit CPU1 through a buffer Z15. A part of signal lines from the control board 600 is connected to a connector J1. Signals applied to the J1 are in turn applied to input ports of the microcomputer unit CPU1 through a buffer BF1 and a chattering removal circuit CH1. Signals from the system control unit 200 are applied to a part of input ports of the CPU1. The display control circuit 500 is connected other ports of the CPU1.

Referring now to FIG. 12b, the illustrated circuitry makes the control of the pressure ON/OFF controlling solenoid valves 132, 138, 134 and 140 as well as the pressure compensating solenoid valves 135, 141, 136 and 142. This entire circuitry is controlled by a microcomputer unit CPU2. Energization of solenoids for the solenoid valves 132, 138, 134 and 140 are controlled by solid state relays SSR5, SSR6, SSR7 and SSR8, respectively, which relays are controlled by the corresponding output ports of the microcomputer unit CPU2.

Driver circuits DV1, DV2, DV3 and DV4 are connected in parallel to those output ports of the CPU2 used for controlling the solid state relays SSR5, SSR6, SSR7 and SSR8, respectively. The driver circuits DV1, DV2, DV3 and DV4 have all the same construction.

A part of signal lines from the control board 600 is connected to a connector J6. Signals applied to the J6 are in turn applied to input ports of the microcomputer unit CPU2 through a buffer BF2 and a chattering removal circuit CH2. To other input ports of the CPU2 are connected the system control unit 200 and the display control unit 500.

The driver circuit DV1 will be now described. Designated at TG is a trigger circuit for detecting the falling of an input signal, and at TM1 and TM2 are timers.

Figure 12C:
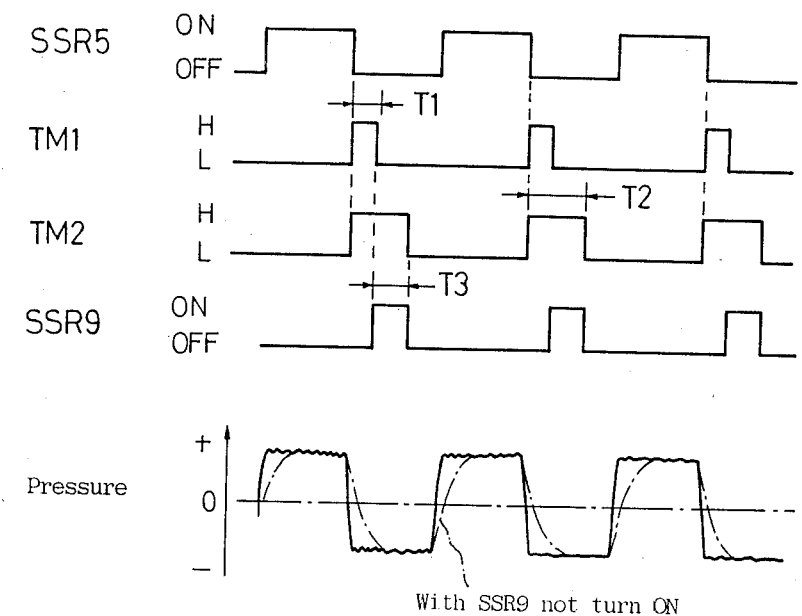

The operating timing, etc. of the driver circuit DV1 is shown in FIG. 12c. Referring to FIG. 12c, the solid state relay SSR5 repeats its ON/OFF operation at a predetermined period, and the solenoid valve 132 is opened and closed correspondingly. The timers TM1 and TM2 are triggered by the falling of the signal for controlling the SSR5. An output level of the TM1 is inverted to H upon triggering and then holds H for a period of T1 from that inversion. The TM2 is also triggered to be inverted to H and then holds H for a period of T2. T1 and T2 are selected to meet $T1 < T2$.

The solid state relay SSR9 for controlling the solenoid valve 135 is turned when the output level of TM1 is L and the output level of TM2 is H, i.e., only in a period of $T3 = (T2 - T3)$. Timing of T3 is within the period where the SSR5 is turned OFF, i.e., the solenoid valve 132 is closed, so that the higher pressure from the compressor 71 will never be directly applied to the artificial heart. Although the pressure at the output terminal of the solenoid valve 131 becomes somewhat higher than the set pressure after opening of the solenoid valve 135, the pressure on the artificial heart side will never become higher than the set pressure because the output terminal pressure of the solenoid 131 is lowered below the predetermined pressure immediately after subsequent opening of the solenoid valve 132. In this embodiment, there is provided to accumulator at the pressure output terminals of the pressure adjusting valves 131, 137, 133 and 139. As an alternative, the solenoid valves 135, 141, 136 and 142 are opened at a predetermined timing during the closed period of the solenoid valves 132, 138, 134 and 140, respectively, whereby the pressure waveform having the sharp rising as shown in FIG. 12c appears in the artificial heart. If the pressure compensating solenoid valves 135, 141, 136 and 142 are not opened, the rising of the pressure waveform will be delayed as seen from a one-dot chain line. Although the pressure compensating solenoid valves are provided in both positive and negative system in the illustrated embodiment, it is found that the satisfactory result can be attained in practice even in case where those solenoid valves are provided in the positive pressure system only.

Figure 13:
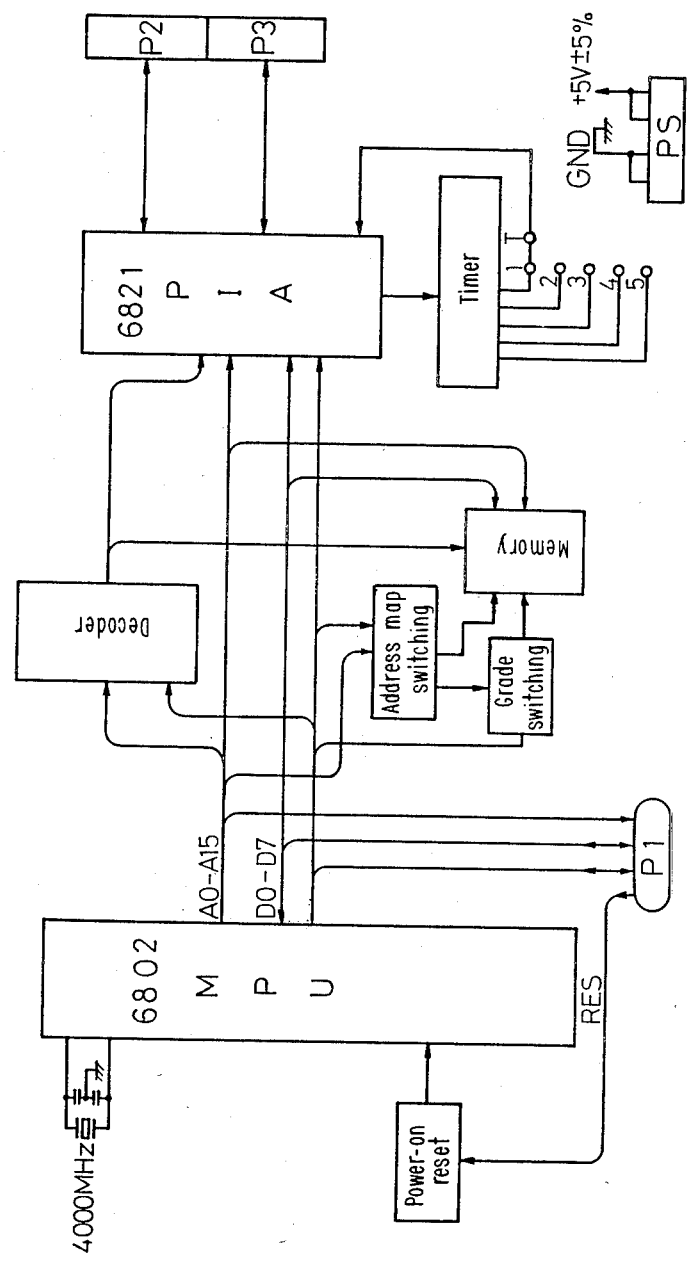
FIG. 13 is a block diagram showing the configuration of microcomputers CPU1 and CPU2.

The microcomputer units CPU1 and CPU2 used in this embodiment are of single board microcomputer units H62SCO1 manufactured by Hitachi Ltd. The summary configuration of H62SCO1 is shown in FIG. 13. Refering to FIG. 13, each unit comprises a microprocessor 6802, I/O ports, timer, RAM, ROM, etc.

Figure 14:
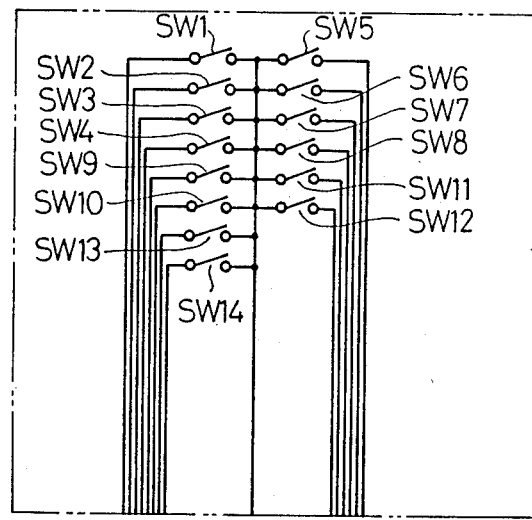
FIG. 14 is an electrical circuit diagram showing the configuration of a control board 600.

FIG. 14 shows the configuration of the control board 600. Referring now to FIG. 14, switches SW1, SW2, SW3, SW4, SW5, SW6, SW7 and SW8 serve to issue instructions for pressure setting and are switches for instructing lefthand positive pressure up, lefthand positive pressure down, lefthand negative pressure up, lefthand negative pressure down, righthand positive pressure up, righthand positive pressure down, righthand negative pressure up and righthand negative pressure down, respectively. Switches SW9, SW10, SW11 and SW12 serve to set the duty ratio of the positive pressure to the negative pressure applied to the artificial heart, and are switches for instructing lefthand duty ratio up, lefthand duty ratio down, righthand duty ratio up and righthand duty ratio down, respectively. Designated at SW13 and SW14 are switches for instructing up and down in heart rate, respectively.

Figure 15:
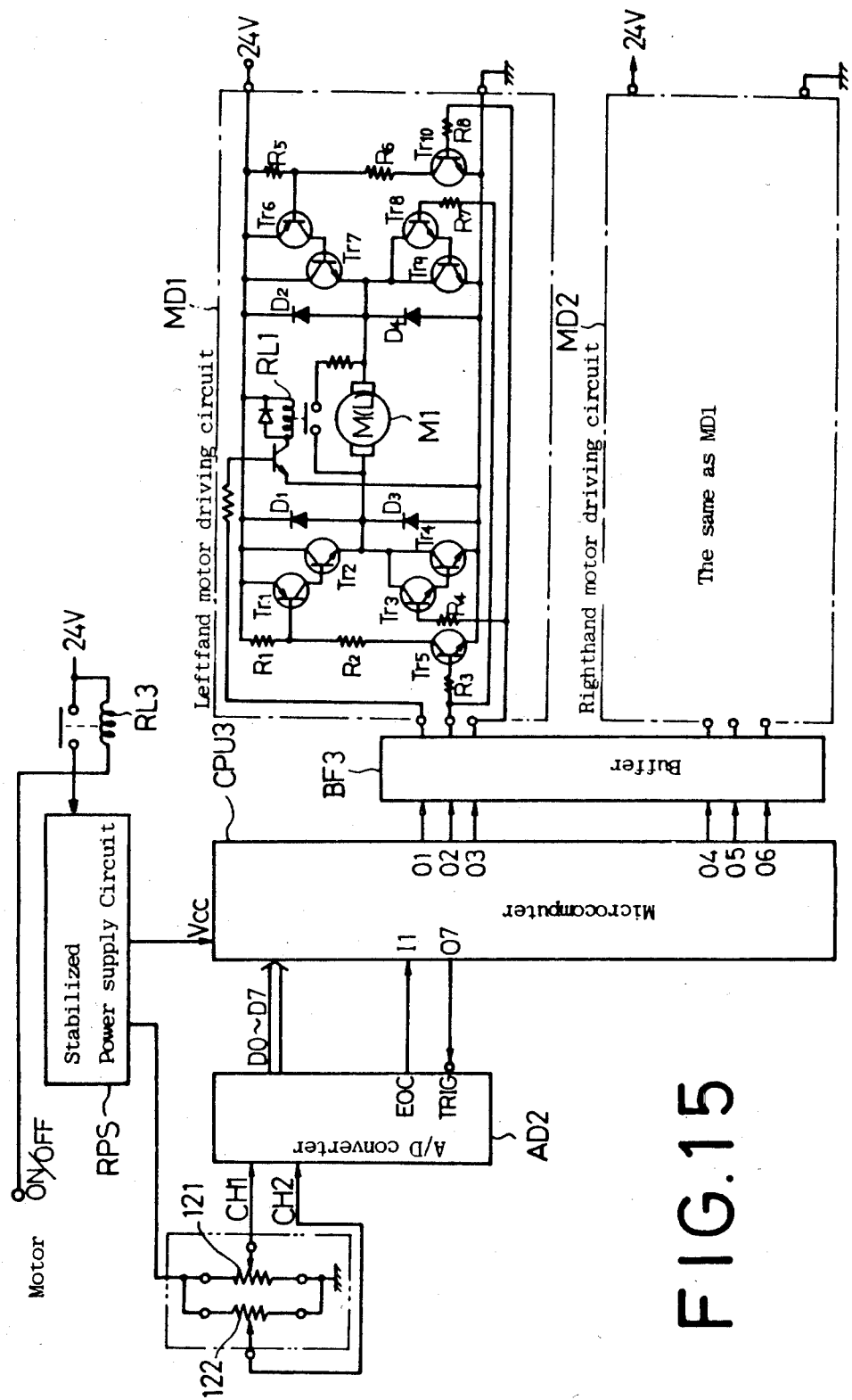
FIG. 15 is a block diagram of a wheelchair driving motor control unit 75 shown in FIG. 10.

FIG. 15 shows the details of the wheelchair driving motor control unit 75 in FIG. 10. Referring now to FIG. 15, the wheelchair driving motors M1 and M2 are connected to independent driving circuits MD1 and MD2, respectively. The driving circuits MD1 and MD2 are each of a H-type driving circuit and, when either one of switching elements locating on a diagonal line, electrical current is caused to flow into an armature of the motor in a predetermined direction so as to rotate it in a predetermined direction.

The contact of a relay RL1 is connected in parallel to an armature of the motor M1. This contact is a normally closed type. Thus, the contact is opened when the relay RL1 is in the ON state, but closed when it is turned OFF to effect the dynamic brake. The motor M2 also includes a similar brake circuit.

Both motor driving circuits MD1 and MD2 are controlled by a microcomputer CPU3. The motor driving circuit MD1 is connected to output ports 01, 02 and 03 of the CPU3 through a buffer BF3, while the motor driving circuit MD2 is connected to output ports 04, 05 and 06 of the CPU3 through a buffer BF3. Power source Vcc for the microcomputer CPU3 is supplied from a stabilized power supply circuit RPS. A battery of 24 V is connected to an input terminal of the stabilized power supply circuit RPS through a relay RL3. The relay RL3 is controlled by the system control unit 200.

Sliders of two potentiometers 121 and 122 connected to the control lever 58 are connected to first and second channels CH1 and CH2 of an analog/digital converter AD2, respectively, and output terminals D0 through D7 of the AD2 are connected to input ports of the microcomputer CPU3. The predetermined constnat voltage is applied to both potentiometers 121 and 122 from the stabilized power supply circuit RPS.

Figure 16:
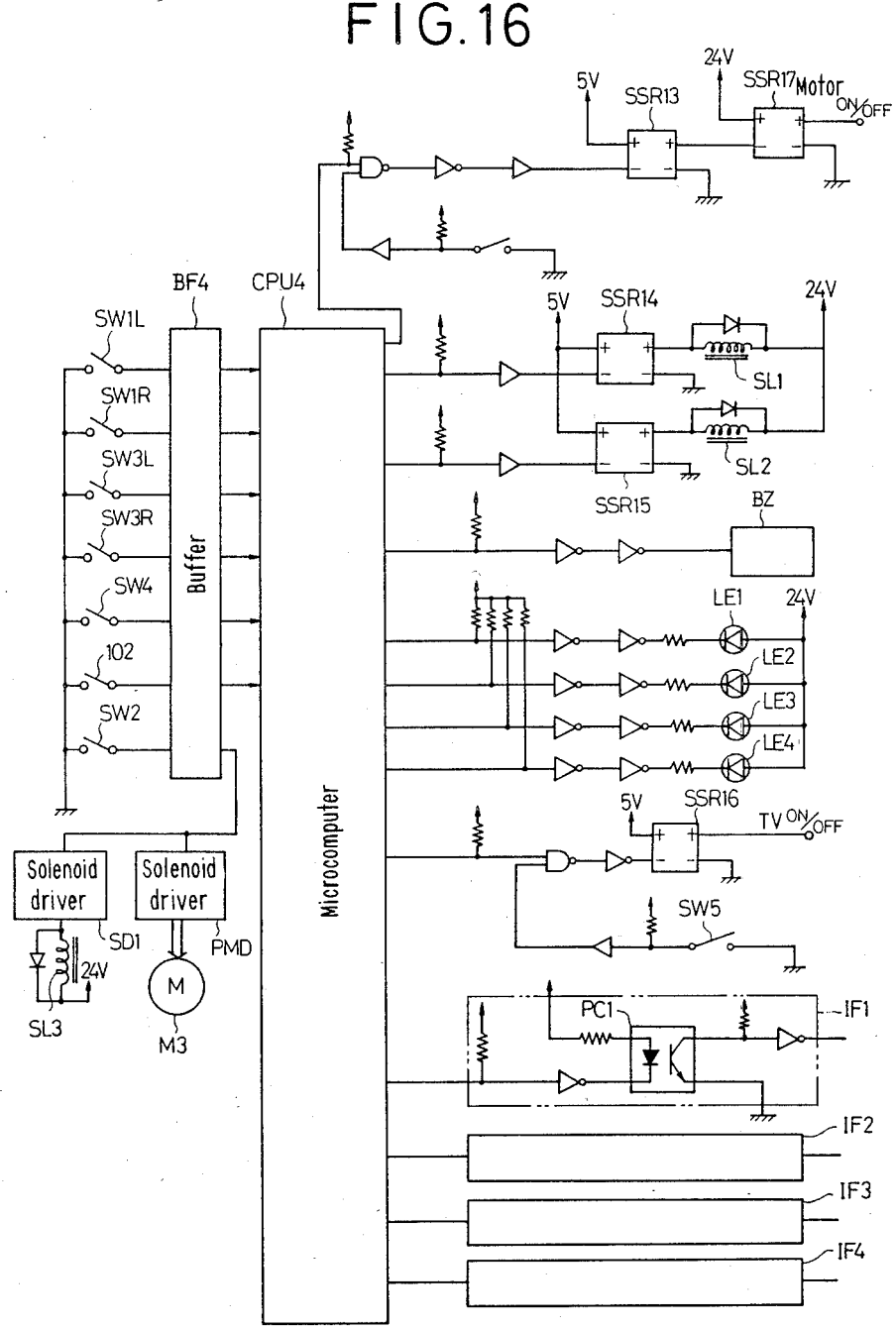
FIG. 16 is a block diagram of a system control unit 200 shown in FIG. 10.

FIG. 16 shows the detail configuration of the system control unit 200 in FIG. 10. Referring now to FIG. 16, the system control unit 200 is controlled by a microcomputer CPU4. To input ports of the CPU4 are connected various switches SW1L, SW1R, SW3L, SW3R, SW4 and 102 through a buffer BF4.

The reel taking-up instruction switch SW2 is connected to a pulse motor driver PMD and a solenoid driver SD1 through the buffer BF4. The PMD drives a reel taking-up motor M3, while the SD1 drives a solenoid SL3 of the electromagnetic actuator 97. A circuit comprising solid state relays SSR13, SSR17, etc. connected to an output port of the CPU4 serves to drive the power supply relay RL3 shown in FIG. 15. Solid state relays SSR14 and SSR15 connected to output ports of the CPU4 serve to energize solenoids of the electromagnetic actuators 114 for locking the left and right armrests.

Designated at BZ is a warning buzzer. LE1 and LE2 denote light emitting diodes for indicating an alarm in the artificial heart system and provided in the alarm display 59 shown in FIG. 2a. LE3 and LE4 denote light emitting diodes for indicating an alarm in the wheelchair system and are provided in the alarm display 60. The light emitting diodes LE1 and LE3 emit a red color light, while the diodes LE2 and LE4 emit a green color light.

A solid state relay SSR16 connected to an output port of the CPU4 makes the ON/OFF control of power source for the monitor television TV. A switch SW5 is a manual switch for turning ON/OFF the monitor television TV. Designated at IF1, IF2, IF3 and IF4 are interface circuits for transmitting signals to other circuits. The IF1 and IF2 are connected to the CPU1, while the IF3 and IF4 are connected to the CPU3. Those interface circuits IF1, IF2, IF3 and IF4 are each composed of an inverter, photo coupler PC1, etc.

Figure 17C:
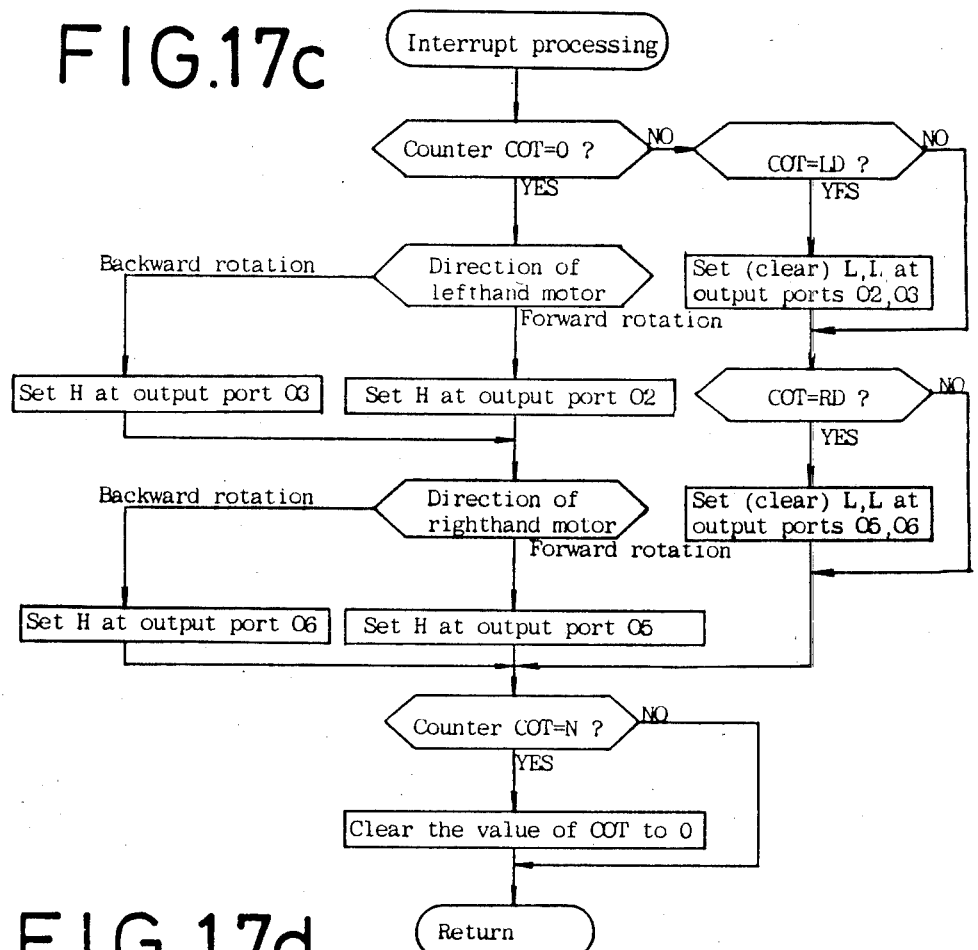
Figure 17D:
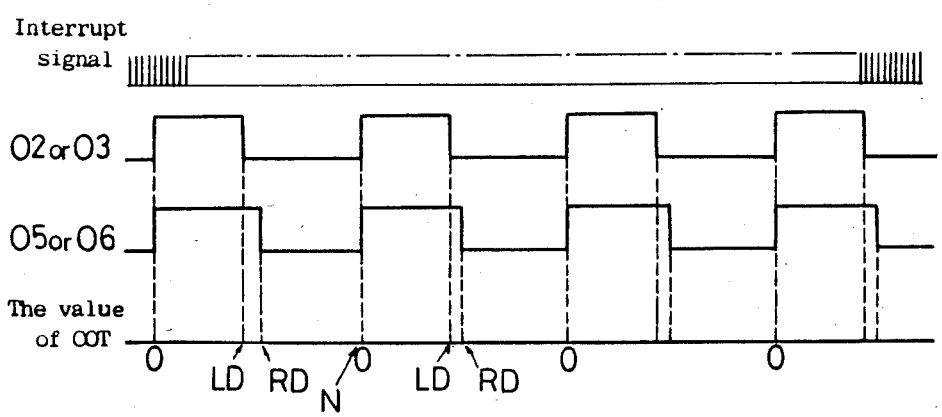
FIG. 17d is a timing chart showing operation of the wheelchair driving motor control unit 75.

FIGS. 17a, 17b and 17c show summary operation of the microcomputer CPU3 in FIG. 15, and FIG. 17d shows one example of the operating timing. FIG. 17a denotes a main routine, FIG. 17b denotes a voltage sampling subroutine and FIG. 17c denotes an interrupt processing routine.

The summary operation thereof will be now described. In this embodiment, to make small loss of the power, both direct current motors M1 and M2 are subjected to the switching control and a pulse width of the switching pulses is modulated in accordance with the positions of the potentiometers 121 and 122 connected to the control lever 58, thereby to set a motor speed.

When positive pulses are applied to the output ports of the CPU3, both motors M1 and M2 are driven forwards, and when positive pulses are applied to the output ports 03 and 06 thereof, both motors M1 and M2 are driven backwards. In this embodiment, the wheelchair moves forwards when both M1 and M2 are driven forwards at the same speed, moves rearwards when both are driven backwards at the same speed, and curves or turns forwards or rearwards in cases other than the aboves. When both motors M1 and M2 are not driven, the relays RL1, etc. are turned OFF and the armatures of the motors M1 and M2 are short-circuited to effect the brake.

By referring to FIGS. 17a, 17b, 17c and 17d, the operation of the CPU3 will be now described in order. First, when the power supply is turned ON, i.e., when the relay RL3 shown in FIG. 15 is turned ON, the CPU3 set the individual output ports at their levels, clears the content of the random access memory (RAM) and stores initial parameters having been previously stored in the read-only memory (ROM) into registers (memories) allocated to the individual parameters. In the initial state, the output ports 01 and 04 of the CPU3 are set at L, thus coming into the braking mode. Also, interrupt is inhibited in this state.

When the CPU is set interruptible, the timer issues an interrupt demand for each predetermined period of time. If interrupt is effected, the CPU3 executes the processing as shown in FIG. 17c. This proccessing will be described later in detail.

Then, the CPU3 reads the slider potentials of the potentiometers 121 and 122 connected to the running control lever 58. The detailed of this sampling processing is shown in FIG. 17b. As a result of the sampling, when the present potential is different from the previously sampled value, i.e., when the control lever 58 has been moved, the CPU3 updates the speed instruction data for the motors and then operates as follows.

By comparing the speed instruction data with predetermined values, it is judged whether driving or braking. More specifically, in the illustrated embodiment the constant voltage of 12 V is applied to one ends of the potentiometers 121 and 122, and the slider potential assumes about 6 V when the control lever 58 is in its neutral position (stoppage position). Therefore, since a range of about 6±0.2 V is assumed as a stoppage region, it is arranged that the speed instruction data is compared with the data representing the upper and lower limits of that stoppage region (i.e. predetermined values). The voltage higher than the values corresponding to the stoppage region represents the forward driving, while the voltage lower than those values represent the backward driving.

When the speed instruction data is at a stoppage level (i.e., below the predetermined values), interrupt is inhibited, a low level L is set to the output ports 02, 03, 05 and 06 to inhibit driving of the motors, and a low level L is set to the output ports 01 and 04, thus setting the braking mode and setting the braking flag to "1".

On the other hand, when the speed instruction data is at a driving level (i.e., above the predetermined values), widths (time period) LD and RD of pulses for driving the motors M1 and M2 are calculated based on the speed instruction data. If the braking flag is set to "1", the braking mode is released as follows. More specifically, the value of the counter COT is cleared to 0, the output ports 01 and 04 are set to H (the relay RL1 ON) and the braking flag is cleared to "0" so as to allow the interrupt demand.

The voltage sampling processing (FIG. 17b) will be now described. First, the input channel designation for the A/D converter AD2 is set to CH1 (output voltage of the potentiometer 121), the A/D conversion start instruction (TRIG) is issued and then it waits for the end A/D conversion (EOC), i.e., until EOC will be output. Upon the end of conversion, the converted data is read and stored in the predetermined register. Subsequently, the input channel designation is set to CH2 (output voltage of 122), the A/D conversion start instruction is issued and then it waits for the end of A/D conversion. Upon the end of conversion, the converted data is read and stored in the predetermined register.

The interrupt processing of FIG. 17c will be now described by referring to the operating timing of FIG. 17d. The counter COT serves to count a time and, more concretely, is formed of an N-notation counter which counts as follows; 0, 1, 2, ... N−1, N, 0, 1 ..., which is counted up one by one every when the interrupt processing is executed. The time corresponding to the value N represents one period of the motor driving pulses.

When the value of the counter COT becomes 0, the output port determined in accordance with the driving directions of the motors is set to a high level H. In other words, in case of the lefthand motor M1, the output port 02 is set to H for its forward rotation and the output port 03 is set to H for its backward rotation. In case of the righthand motor M2, the output ports 05 or 06 is set to H for its forward or backward rotation, respectively. The pulses for driving the M1 and those for driving the M2 have the same timing.

When the value of the counter COT equals to the lefthand motor energizing pulse width LD, both output ports 02 and 03 are set to L, and when the value of the counter COT equals to the righthand motor energization pulse width RD, both output ports 05 and 06 are set to L.

Therefore, the pulses for energizing the motor M1 are set to H during the time the value of the COT assumes 0 through LD, and are set to L (i.e., M1 is deenergized) during the time except for the above. The pulses for energizing the motor M2 are set to H during the time the value of the COT assumes 0 through RD, and are set to L during the time except for the above. Since both motors M1 and M2 are rotated at a speed in accordance with the power applied thereto, namely, the duty ratio of the time period for energization to that for deenergization, the motor speed can be varied by changing the values of LD and RD.

Figure 18A:
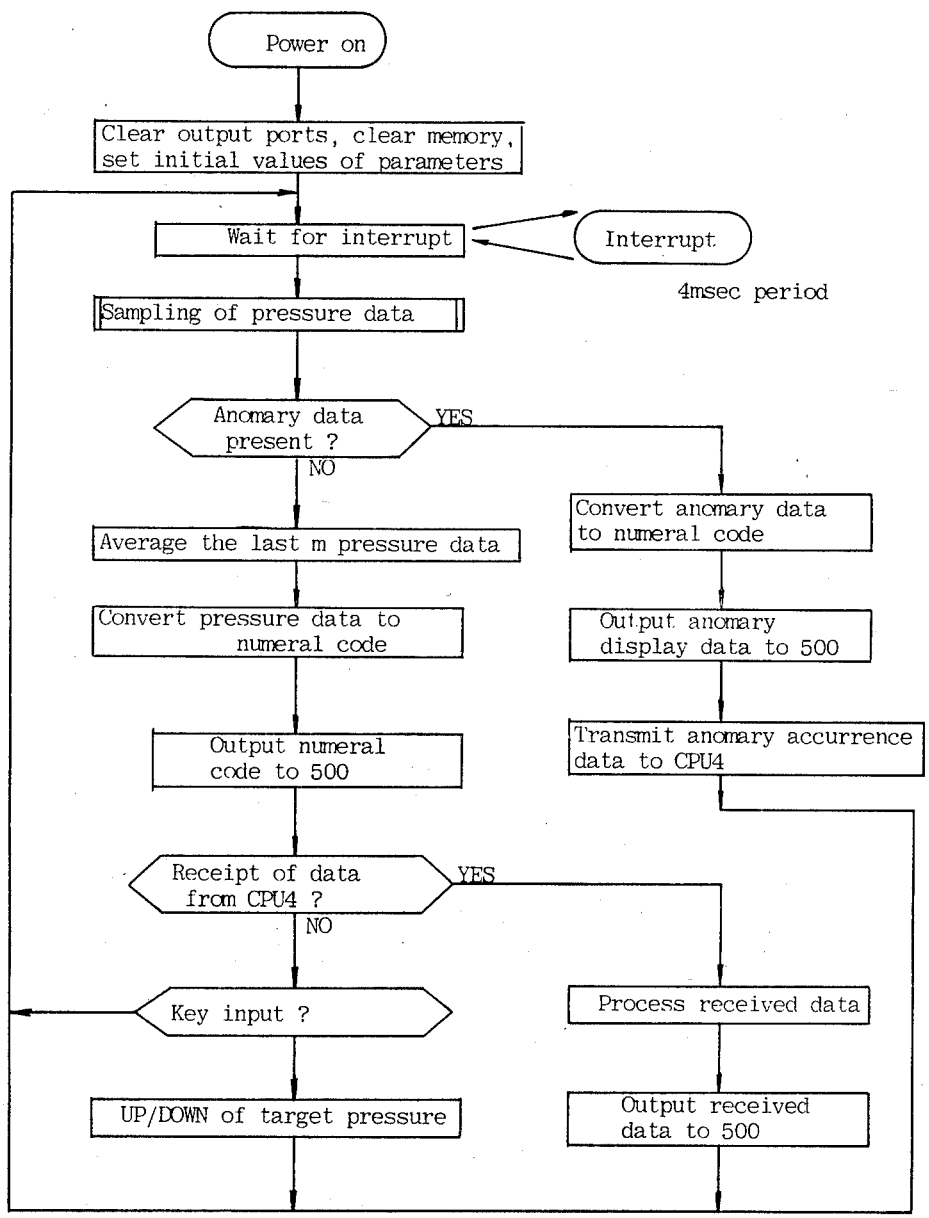
FIGS. 18a and 18b are flow charts showing summary operation of the microcomputer unit CPU1.
Figure 18B:
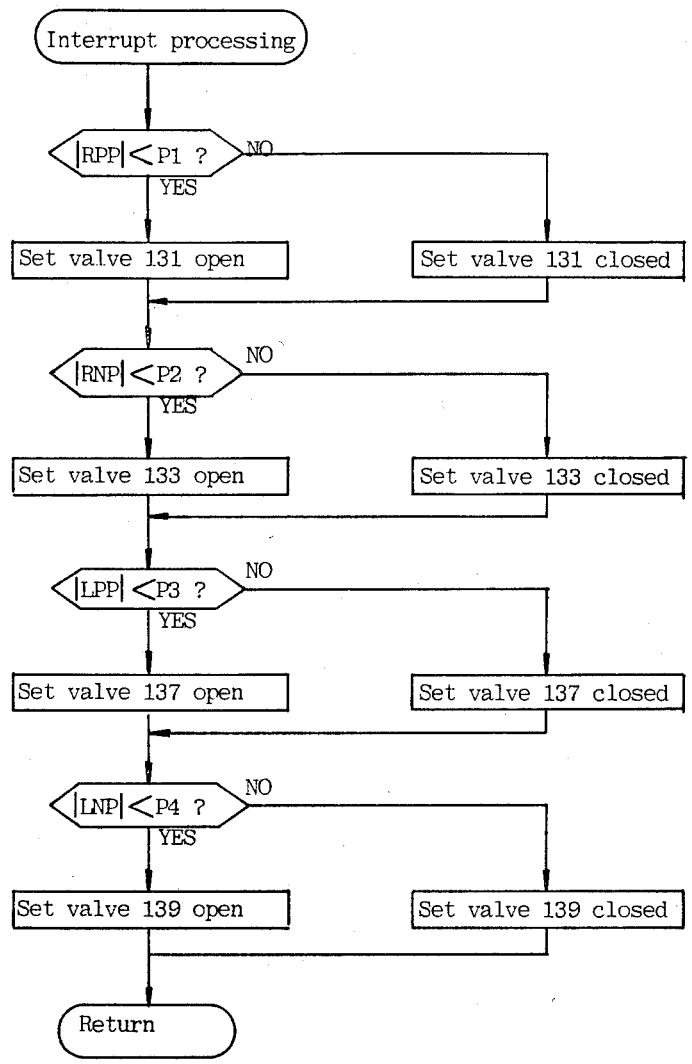

FIGS. 18a and 18b show summary operation of the microcomputer CPU1 in FIG. 12a. FIG. 18a denotes a main routine and FIG. 18b denotes an interrupt processing routine. The description will be now made by referring to FIGS. 18a and 18b.

First, when the power supply is turned ON, the individual output ports are set at their initial levels, the content of the random access memory (RAM) is cleared and the data having been previously stored in the read-only memory (ROM) is read out therefrom to set the initial values to the parameters. The parameters for the CPU1 are a righthand positive pressure target value P1, righthand negative pressure target value P2, lefthand positive pressure target value P3, lefthand negative pressure target value P4, etc. In this embodiment, the initial values of those pressures P1, P2, P3 and P4 are set at +30, −30, +100 and −50 (mmHg), respectively.

After the above processing, interrupt becomes allowable. In this embodiment, interrupts are periodically occurred by the internal timer at a period of 4 msec. After it waits for the interrupt demand, sampling of the pressure data is performed. This sampling processing is similar to that shown in FIG. 17b. The difference are in that there are four parameters to be sampled, outputs RPP, RNP, LPP and LNP from the four pressure sensors, and that since the bit number of the data is 12 bits, the read processing is performed two times for each sampling.

The sampled pressure data is checked to judge the presence or absence of anomaly data. In other words, when the detected pressure is abnormally different from the target value, this is regarded as anomaly. It is to be noted that, in this embodiment, the pressure compensating solenoid valves 135, 141, 136 and 142 are provided, thus resulting in a possibility the pressure becomes relatively so large temporarily, but this possibility is masked by making sampling several times and then averaging the plural pressure data thus sampled.

Should there occur any anomaly, the anomaly data is converted to the numeral code data. Then, the anomaly display data indicating that numeral code data and the part where the anomaly has occurred, is output to the display control unit 500 so as to display them on the monitor television TV. Also, the anomaly occurrence code data is transferred in the form of serial data to the microcomputer CPU4 in the system control unit.

If there is no anomaly, the last m pressure data having been stored in the random access memory are averaged. The averaged data is converted to the numeral code, which is sent to the display control unit 500. When the microcomputer CPU4 in the system control unit is transmitting data, the data is received and this received data is also sent to the display control unit 500. With the control board 600 being connected, the states of keys are read. If there is any key-in operation, the value of the righthand positive target pressure P1, righthand negative target pressure P2, lefthand positive target pressure P3 or the lefthand negative target pressure P4 is updated stepwisely by a predetermined amount for each time in accordance with the key operated. Incidentally, since the upper and lower limit is preset, it is impossible to make pressure setting out of such a limit range.

The interrupt processing shown in FIG. 18b will be now described. First, the positive pressure RPP in the righthand artificial heart driving system is checked. When it is lower than the predetermined pressure P1, the pressure adjusting valve 131 is set open, and in the case except for the above, the valve 131 is set closed. Subsequently, the negative pressure RNP in the righthand artificial heart driving system is checked. When the (absolute) value of RNP is lower than P2, the pressure adjusting valve 133 is set open, and if not so, the valve 133 is set closed. Next, the positive pressure LPP and the negative pressure LNP in the lefthand artificial heart driving system are compared with P3 and P4, respectively, and the pressure adjusting valve 137 or 139 is set open or closed. Differently stated, it is so arranged in this embodiment that the pressure adjusting valve is opened only when the detected pressure (absolute value) is lower than the target pressure.

Figure 19A:
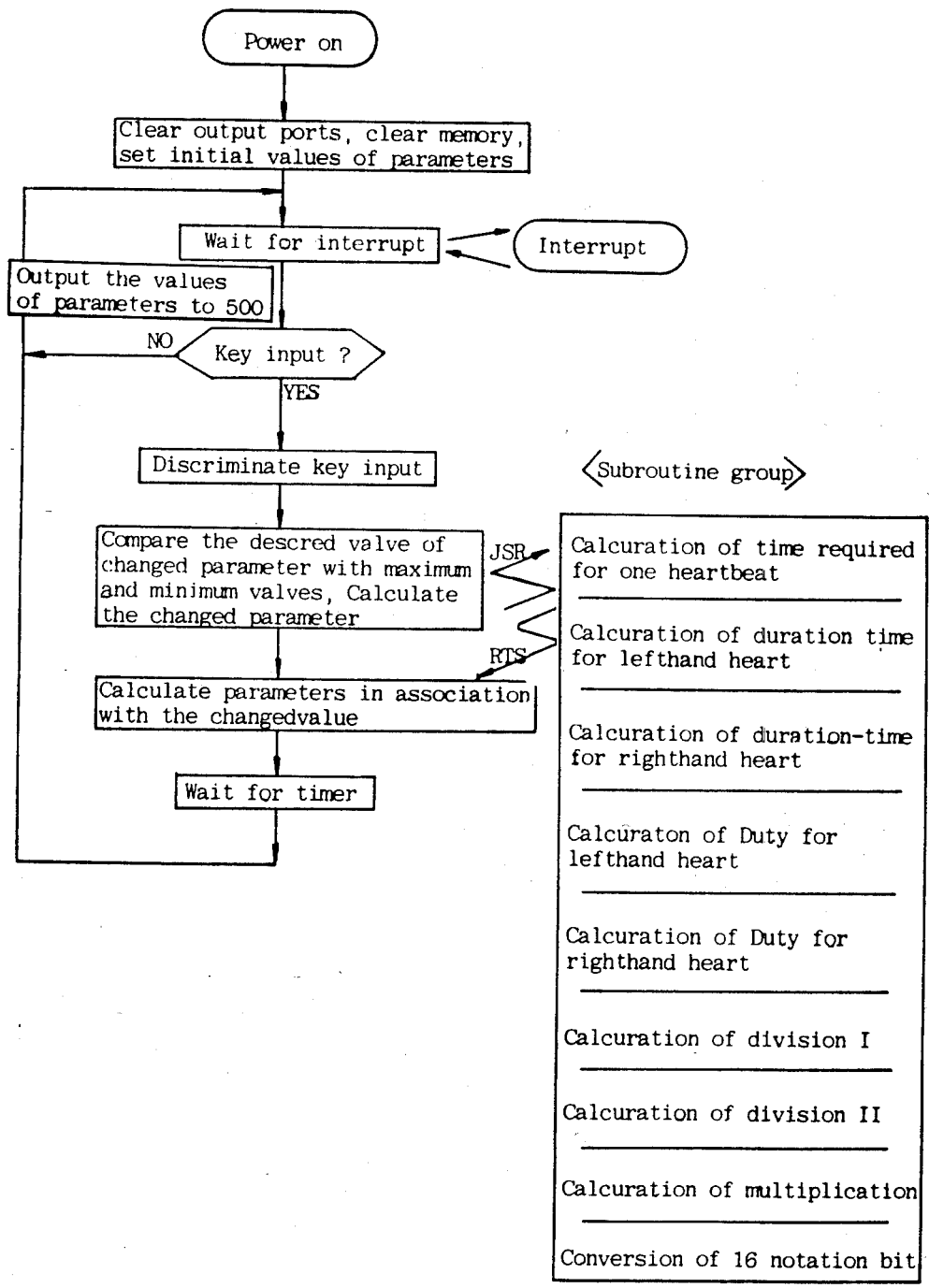
FIGS. 19a and 19b are flow charts showing summary operation of the microcomputer unit CPU2.
Figure 19B:
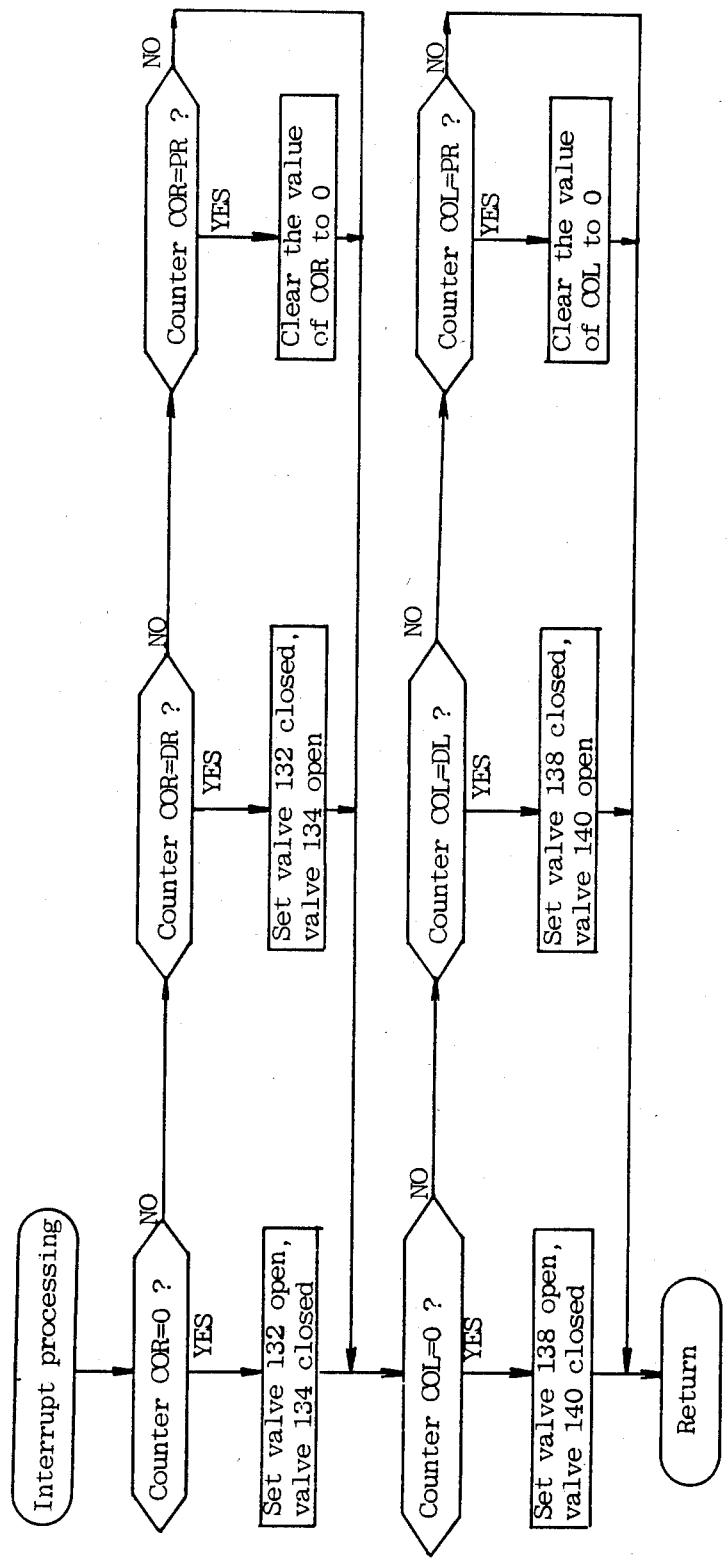

Summary operation of the microcomputer CPU2 in FIG. 12b is shown in FIGS. 19a and 19b. FIG. 19a denotes a main routine and FIG. 19b denotes an interrupt processing routine. The description will be now made by referring to FIGS. 19a and 19b.

First, when the power supply is turned ON, the microcomputer CPU2 sets the output ports at their initial levels, clears the content of the random access memory (RAM) and reads out the values having been previously stored in the read-only memory (ROM) to set the parameters at their initial values.

The parameters for the CPU2 are a heart rate PR, duty of the lefthand artificial heart DL, duty of the righthand artificial heart DR, etc. In this embodiment, the initial values of those parameters PR, DL and DR are set at 100 rpm, 45% (duration time 270 ms) and 55% (duration time 330 ms), respectively.

Subsequently, the CPU2 executes the processing loop including such processings as interrupt waiting, check of a key input from the control board, parameter display, etc. If there occurs any key input, the kind of the input key is judged, comparison of the desired value of the parameter to be changed with the upper and lower limit values as well as calculation thereof is performed, and arithmetic processing of those parameters in association with the changed parameter is carried out. These processings are progressed under execution of the related various subroutines.

The interrupt processing will be now described. The value of both counters COR and COL are each counted up for each interrupt processing. When the counted value reaches PR (parameter of time determined by the heart rate), it is cleared to "0". When the value of the counter COR becomes 0, the valves 132 and 134 are set open and closed (positive pressure applying mode), respectively. When the value of the counter COR becomes equal to the value DR of the duty parameter, the valves 132 and 134 are set closed and open (negative pressure applying mode), respectively. After the above processing, the counter COR is counted up.

Likewise, when the value of the counter COL becomes 0, the valves 138 and 140 are set open and closed (positive pressure applying mode), respectively, and when the value of the counter COL beocmes equal to the value DL of the duty parameter, the valves 138 and 140 are set closed and open (negative pressure applying mode), respectively.

Figure 20:
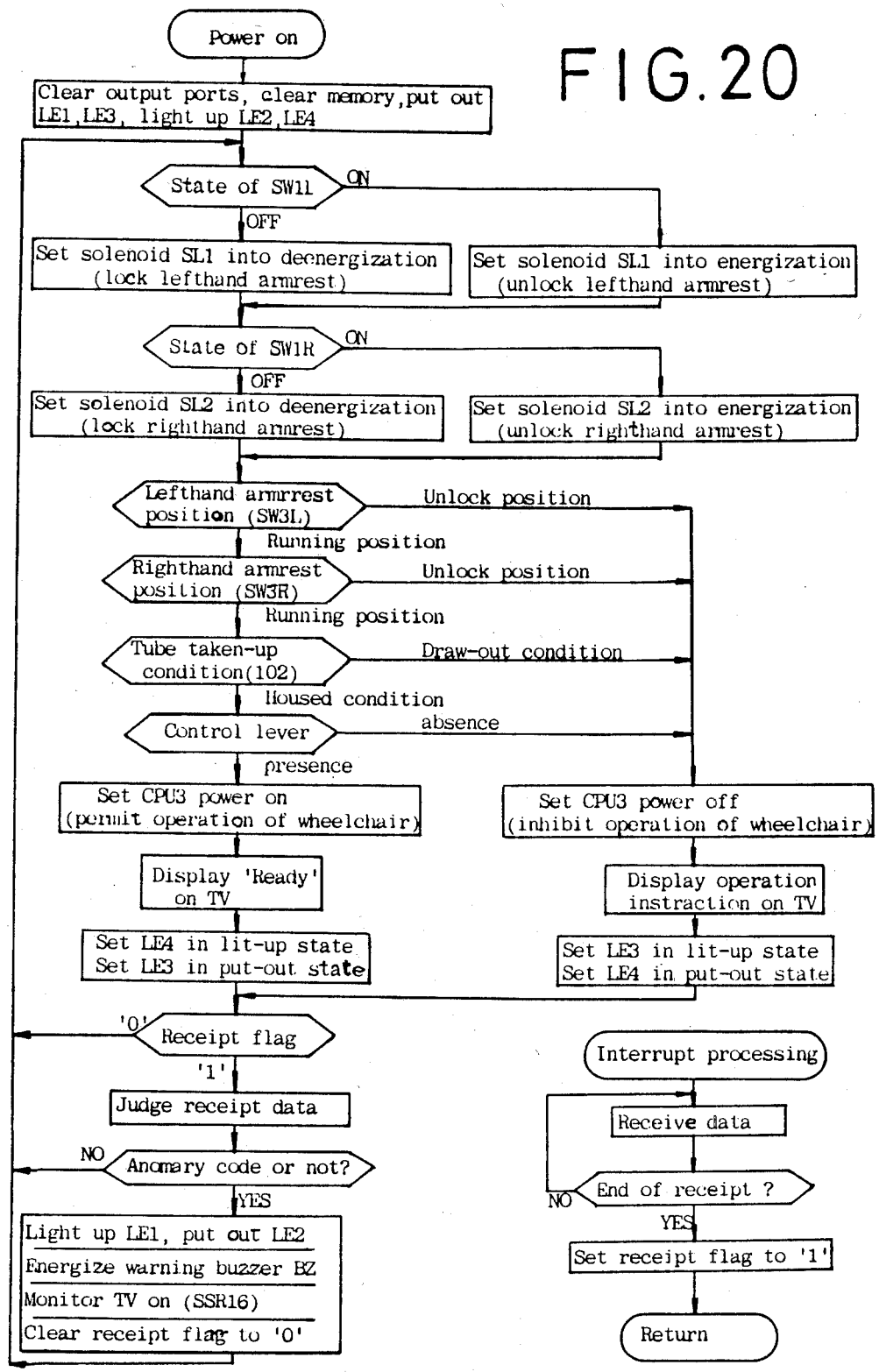
FIG. 20 is a flow chart showing summary operation of a microcomputer unit CPU4.

Summary operation of the microcomputer CPU4 in FIG. 16 is shown in FIG. 20. Referring now to FIG. 20, when the power supply is turned ON, the output ports are set at their initial levels, the content of the random access memory (RAM) is cleared, and the apparatus is set in the initial state in accordance with the program data stored in the read-only memory. This causes the light emitting diodes LE1 and LE3 to be set into deenergization and the light emitting diodes LE2 and LE4 to be set into energization, whereby green color (normal state) is indicated on both anomaly displays 59 and 60 of the wheelchair.

Thereafter, the CPU4 periodically checks the states of various switches and then operates in accordance with the checked states. When the armrest unlocking switches SW1L and SW1R are turned ON, the solenoids SL1 and SL2 of the electromagnetic actuators 114 and set into energization, and when those switches are turned OFF, the solenoids SL1 and SL2 are set into deenergization. Since energization of the solenoid SL1 or SL2 releases the armrest from its locked state, the lefthand or righthand armrest becomes rotatable in a range of 90 degrees. On the other hand, when the armrest is set in the running position with the solenoid being deenergized, it is locked.

Next, the CPU4 checks the states of the lefthand armrest position detecting switch SW3L, righthand armrest position detecting switch SW3R, artificial heart driving tube position detecting switch 102 and the running control lever presence/absence detecting switch SW4.

When the lefthand and righthand armrests 52L and 52R are in the running positions (both SW3L and SW4L ON), the artificial heart driving tubes 57L and 57R are both in the housed condition (102 ON) and the running control lever 58 is fitted in the predetermined position (SW4 ON), it is assumed that the user sits on the wheelchair and wishes to run. Thus, the relay RL3 is turned ON to set ON the power for the wheelchair driving motor control unit 75. At the same time, the data for displaying that the apparatus is in the ready state, is sent to the CPU1 through the interface circuit IF1. The CPU1 transfers the received data to the display control unit.

When the lefthand armrest is in the unlocked position, the righthand armrest is in the unlocked position, the artificial heart driving tubes are in the drawn-out condition, or the running control lever is absent, the relay RL3 is turned OFF to set OFF the power for the wheelchair driving motor control unit 75. As a result, the output ports 01, 02, 03, 04, 05 and 06 of the CPU3 assume a low level L and both motors M1 and M2 are not supplied with the power from the outside, so that operation of the wheelchair is inhibited. At the same time, since the relay RL1 is turned OFF and the contact of RL1 is closed, the armatures of both motors M1 and M2 are short-circuited and the dynamic braking mode is set.

Subsequently, the data for displaying the operating instruction such as "Please set the running control lever", etc. is sent to the CPU1 so as to display it on the monitor television TV. Also, the light emitting diode LE3 is lit up and the LE4 is put out, thereby to indicate red color on the anomaly display 60 for the wheelchair system.

When receiving the data sent from the CPU1, the CPU3 undergoes interrupt and executes the interrupt processing. In this interrupt processing, the CPU3 receives the data through the interface circuit IF2 and sets the receipt flag to "1" upon the completion of receipt. When the receipt flag becomes "1", the received data is judged by the main routine. In the event the anomaly code has been sent, the anomaly processing operation will be performed as follows.

That is, the light emitting diode LE1 is lit up and the LE2 is put out so as to indicate red color (occurrence of anomaly) on the artificial anomaly display 59. At the same time, the warning buzzer BZ is buzzed, the power for the monitor television TV is set ON (SSR16 ON) and the receipt flag is cleared to "0".

Having now fully set forth both structure and operation of preferred embodiment of the concept underlying the present invention, various other embodiments as well as certain variations and modifications of the embodiment herein shown and described will obviously occur to those skilled in the art upon becoming familiar with the underlying concept. It is to be understood, therefore, that with the scope of the appended claims, the invention may be practiced otherwise than as specifically set force herein.

What we claim is:

1. A mobile apparatus for transporting a patient connected to a medical appliance comprising:
a wheelchair;
medical appliance driving means mounted on said wheelchair and comprising; a positive pressure source; a first solenoid valve having an input terminal connected to an output terminal of said positive pressure source; first pressure detecting means for detecting the pressure at an output terminal of said first solenoid valve; a second solenoid valve having an input terminal connected to the output terminal of said first solenoid valve and an output terminal adapted to be connected to said medical appliance; a negative pressure source; a third solenoid valve having an input terminal connected to said negative pressure source; second pressure detecting means for detecting the pressure at an output terminal of said third solenoid valve; a fourth solenoid valve having an input terminal connected to the output terminal of said third solenoid valve and an output terminal adapted to be connected to said medical appliance; and first electronic control means adapted to control opening and closing of said first solenoid valve in response to an output signal from said first pressure detecting means, control opening and closing of said third solenoid valve in response to an output signal from said second pressure detecting means, and to control opening and closing of said second and fourth solenoid valves at predetermined timings, respectively;

electric motor means for driving said wheelchair;

instruction means for controlling energization of said electric motor means;

state detecting means for detecting at least one state of at least one part moveable on said wheel chair, the state of a moveable part of said medical appliance driving means and the state of said instruction means and providing signals indicative of said states; and second electronic control means connected to said state detecting means for energizing said electric motor means in response to operation of said instruction means, and for inhibiting energization of said electric motor means when said state detecting means detects a dangerous state.

2. An apparatus according to claim 1, wherein said instruction means comprises a control lever and a lever supporting means for supporting said lever in a detachable manner, and said state detecting means provides a signal indicative of the state of attachment of said control lever with respect to said lever supporting means.

3. An apparatus for driving a medical appliance according to claim 1, wherein said wheelchair comprises at least one armrest moveable on said wheelchair and lock means for locking said armrest in a predetermined position, and said state detecting means provides a signal indicative of the state of said lock means.

4. An apparatus for driving a medical appliance according to claim 3, wherein said armrest is constructed to be moveable horizontally about a support shaft, and said lock means includes engagement means engaged with said support shaft and an electromagnetic actuator for moving said engagement means out of engagement with said shaft.

5. An apparatus for driving a medical appliance according to claim 1, wherein said medical appliance driving means comprises; flexible tubes connected at one end to said second solenoid valve and said fourth solenoid valve respectively and adapted to be connected at the other ends thereof to said medical appliance; and tube taking-up means for retracting said flexible tubes and wherein said state detecting means provides a signal indicative of the state of retraction of said flexible tubes.

6. An apparatus for driving a medical appliance according to claim 5, wherein said tube taking-up means comprises; a first fixed member having a first bore axially penetrating through the central part thereof and a groove in a position of the outer periphery thereof; a second fixed member having first and second passages formed at positions opposite to said groove of said first fixed member, and fitted to said outer periphery of said first fixed member; a moveable member provided with a third passage formed at a position opposite to said first bore and with a fourth passage formed at a position opposite to said second passage, and fitted to the outer periphery of said second fixed member rotatably relative to the same; and a tube reel rotatable together with said moveable member, the pressure output terminals of said second and fourth solenoid valves being connected to at least one of said first bore and said first passage, and said flexible tubes being connected to at least one of said third and fourth passages.

7. An apparatus for driving a medical appliance according to claim 5, wherein said tube taking-up means includes electric motor means for rotating said tube reel and switch means for controlling energization of said motor.

8. An apparatus for driving a medical appliance according to claim 1, wherein, when energization of said electric motor is inhibited, said second electronic control means short circuits an armature of said electric motor means for braking movement of said wheelchair.

9. An apparatus for driving a medical appliance according to claim 1, wherein said medical appliance driving means includes a fifth solenoid valve connected in parallel to said first solenoid valve and a sixth solenoid valve, and said first electronic control means controls opening and closing of said fifth and sixth solenoid valves according to predetermined timing in synchronous relation with operation of said second and fourth solenoid valve.

10. An apparatus for driving a medical appliance according to claim 9, wherein said first electronic control means comprises means for setting said fifth solenoid valve in the opened state according to a predetermined timing during the time said second solenoid is closed, and means for setting said sixth solenoid valve in the opened state according to a predetermined timing during the time said fourth solenoid valve is closed.

11. An apparatus for driving a medical appliance according to claim 10, wherein said first electronic control means comprises means for setting said fifth solenoid valve in the opened state for a predetermined time shorter than the closing time of said second solenoid valve after the lapse of a predetermined time from closing of said second solenoid valve, and means for setting said sixth solenoid valve in the opened state for a predetermined time shorter than the closing time of said fourth solenoid valve after the lapse of a predetermined time from closing of said fourth solenoid valve.

12. A mobile apparatus for transporting a patient connected to a medical appliance comprising:

a wheelchair;

medical appliance driving means mounted on said wheelchair and comprising; a positive pressure source; a first solenoid valve having an input terminal connected to an output terminal of said positive pressure source; first pressure detecting means for detecting the pressure at an output terminal of said first solenoid valve; a second solenoid valve having an input terminal connected to the output terminal of said first solenoid valve and an output terminal adapted to be connected to said medical appliance through a flexible tube; a negative pressure source; a third solenoid valve having an input terminal connected to said negative pressure source; a fourth solenoid valve having an input terminal connected to an output terminal of said third solenoid valve and an output terminal adapted to be connected to said medical appliance through a flexible tube; and first electronic control means adapted to control opening and closing of said first solenoid valve in response to an output signal from said first pressure detecting means, control opening and closing of said third solenoid valve in response to an output signal from said second pressure detecting means, and to control opening and closing of said second and fourth solenoid valve at predetermined times, respectively;

electric motor means for driving said wheelchair;

instruction means for controlling energization of said electric motor means;

first state detecting means for detecting the state of at least one part moveable on said wheelchair;

second state detecting means for detecting the state of said flexible tube of said medical appliance driving means;

third state detecting means for detecting the state of said instruction means; and second electronic control means connected to said state detecting means for energizing said electric motor in response to operation of said instruction means, and for inhibiting energization of said electric motor when at least one of said first, second and third state detecting means detects a dangerous state.

13. An apparatus for driving a medical appliance according to claim 12, wherein said instruction means comprises a control lever and a lever supporting means for supporting said lever in a detachable manner, and said third state detecting means provides a signal indicative of the state of attachment of said control lever to said lever supporting means.

14. An apparatus for driving a medical appliance according to claim 12, wherein said wheelchair comprises at least one armrest moveable on said wheelchair and lock means for locking said armrest in a predetermined position, and said first state detecting means provides a signal indicative of the state of said lock means.

15. An apparatus for driving a medical appliance according claim 14, wherein said armrest is constructed to be moveable horizontally about a support shaft, and said lock means includes engagement means engaged with said support shaft and an electromagnetic actuator for moving said engagement means out of engagement with said shaft.

16. An apparatus for driving a medical appliance according to claim 12, wherein said medical appliance driving means comprises tube taking-up means for rolling up said flexible tubes, and said second state detecting means generates a signal in accordance with the rolled-up condition of said flexible tubes.

17. An apparatus for driving a medical appliance according to claim 16, wherein said tube taking-up means comprises; a first fixed member having a first bore axially penetrating through the central part thereof and a groove in a portion of the outer periphery thereof; a second fixed member having a first and second passage formed at positions opposite to said groove of said first fixed member, and fitted to said outer periphery of said first fixed member; a moveable member provided with a third passage formed at a position opposite to said first bore and with a fourth passage formed at a position opposite to said second passage, and fitted to the outer periphery of said second fixed member rotatably relative to the same; and a tube reel rotatable together with said moveable member, the pressure output terminals of said second and fourth solenoid valves being connected to at least one of said first bore and said first passage, and said flexible tubes being connected to at least one of said third and fourth passages.

18. An apparatus for driving a medical appliance according to claim 16, wherein said tube taking-up means includes electric motor means for rotating said tube reel and switch means for controlling energization of said motor.

19. An apparatus for driving a medical appliance according to claim 12 wherein said medical appliance driving means comprises tube taking-up means for rolling up said flexible tubes, and said second state detecting means generates a signal in accordance with the rolled-up condition of said flexible tubes.

20. A mobile apparatus for transporting a patient connected to a medical appliance comprising:

a wheelchair;

medical appliance driving means mounted on said wheelchair and comprising; a positive pressure source; a first solenoid valve having an input terminal connected to an output terminal of said positive pressure source; first pressure detecting means for detecting the pressure at an output terminal of said first solenoid valve and an output terminal adapted to be connected to said medical appliance through a flexible tube, a negative pressure source; a third solenoid valve having an input terminal connected to said negative pressure source; a fourth solenoid valve having an input terminal connected to an output terminal of said third solenoid valve and an output terminal adapted to be connected to said medical appliance through a flexible tube; and first electronic control means adapted to control opening and closing of said first solenoid valve in response to an output signal from said first pressure detecting means, control opening and closing of said third solenoid valve in response to an output signal from said second pressure detecting means, and to control opening and closing of said second and fourth solenoid valves at predetermined timings, respectively; and a tube taking-up means for rolling up said flexible tubes;

electric motor means for rotating said wheelchair;

instruction means for controlling energization of said electric motor means;

first state detecting means for detecting the state of at least one part moveable on said wheelchair;

second state detecting means for detecting the rolled up state of said flexible tubes of said medical appliance driving means;

third state detecting means for detecting the state of said instruction means; and second electronic control means connected to said state detecting means for energizing said electric motor in response to operation of said instruction means, and for inhibiting energization of said electric motor when at least one of said first, second and third state detecting means detects a dangerous state.

21. A mobile apparatus for transporting a patient connected to a medical appliance comprising:

a wheelchair;

medical appliance driving means mounted on said wheelchair and comprising; a positive pressure source; a first solenoid valve having an input terminal connected to an output terminal of said positive pressure source; first pressure detecting means for detecting the pressure at an output terminal of said first solenoid valve; a second solenoid valve having an input terminal connected to the output terminal of said first solenoid valve and an output terminal adapted to be connected to said medical appliance through a flexible tube; a negative pressure source; a third solenoid valve having an input terminal connected to said negative pressure source; a fourth solenoid valve having an iput terminal connected to an output terminal of said third solenoid valve and an output terminal adapted to be connected to said medical appliance through a flexible tube; a fifth solenoid valve connected in parallel to said first solenoid valve and a sixth solenoid valve connected in parallel to said third solenoid valve; and first electronic control means adapted to control opening and closing of said first solenoid valve in response to an output signal from said first pressure detecting means, control opening and closing of said third solenoid valve in response to an output signal from said second pressure detecting means, control opening and closing of said second and fourth solenoid valves at predetermined timings, respectively, and to control said fifth and sixth solenoid valves at the predetermined timing in synchronous relation with operation of said second and fourth solenoid valve;

electric motor means for driving said wheelchair;

instruction means for instructing energization of said electric motor;

first state detecting means for detecting the state of at least one part moveable on said wheelchair;

second state detecting means for detecting the state of said flexible tube of said medical appliance driving means;

third state detecting means for detecting the state of said running instruction means; and second electronic control means connected to said state detecting means for energizing said electric motor in response to operation of said instruction means, and for inhibiting energization of said electric motor means when at least one of said first, second and third state detecting means detects a dangerous state.

* * * * *